(12) United States Patent
Verkaik et al.

(10) Patent No.: US 11,751,771 B2
(45) Date of Patent: Sep. 12, 2023

(54) EXTRAVASCULAR CUFF

(71) Applicants: RTM Vital Signs LLC, Fort Washington, PA (US); Thomas Jefferson University, Philadelphia, PA (US)

(72) Inventors: Josiah Verkaik, Boise, ID (US); Jeffrey I. Joseph, Narberth, PA (US); Noud Van Helmond, Philadelphia, PA (US)

(73) Assignees: RTM Vital Signs, LLC, Philadelphia, PA (US); Thomas Jefferson University, Philadelphia, PA (US)

( * ) Notice: Subject to any disclaimer, the term of this patent is extended or adjusted under 35 U.S.C. 154(b) by 1129 days.

(21) Appl. No.: 16/423,653

(22) Filed: May 28, 2019

(65) Prior Publication Data
US 2019/0365249 A1  Dec. 5, 2019

Related U.S. Application Data

(60) Provisional application No. 62/750,956, filed on Oct. 26, 2018, provisional application No. 62/678,777, filed on May 31, 2018.

(51) Int. Cl.
*A61B 5/0215* (2006.01)
*A61B 5/00* (2006.01)

(52) U.S. Cl.
CPC .......... *A61B 5/0215* (2013.01); *A61B 5/6876* (2013.01); *A61B 2562/028* (2013.01); *A61B 2562/16* (2013.01); *A61B 2562/164* (2013.01); *A61B 2562/168* (2013.01)

(58) Field of Classification Search
None
See application file for complete search history.

(56) References Cited

U.S. PATENT DOCUMENTS

| | | |
|---|---|---|
| 4,398,542 A | 8/1983 | Cunningham et al. |
| 4,592,747 A | 6/1986 | Pool |
| 4,825,876 A | 5/1989 | Beard |
| 4,881,939 A | 11/1989 | Newman |
| 4,920,972 A | 5/1990 | Frank et al. |
| 5,044,203 A | 9/1991 | Wiest et al. |
| 5,722,414 A | 3/1998 | Archibald et al. |

(Continued)

FOREIGN PATENT DOCUMENTS

| | | | | |
|---|---|---|---|---|
| JP | H03112534 A | * | 5/1991 | ............. A61B 5/022 |
| JP | H03112534 A | | 5/1991 | |

*Primary Examiner* — Meredith Weare
(74) *Attorney, Agent, or Firm* — Christopher & Weisberg, P.A.

(57) ABSTRACT

An implantable extravascular pressure sensing system including a cuff having a first brace portion, a second brace portion, and a plurality of biasing members movably coupling the first brace portion and the second brace portion to each other, the first brace portion defining a fluid chamber, the fluid chamber defining a recessed aperture, a flexible diaphragm coupled to the fluid chamber and sealing the recessed aperture, a fluid disposed within the fluid chamber for exhibiting a hydraulic pressure in communication with the flexible diaphragm, and a pressure sensor coupled to the first brace portion, the pressure sensor being configured to measure a change in the hydraulic pressure when a force is imparted on the flexible diaphragm.

11 Claims, 21 Drawing Sheets

(56) References Cited

U.S. PATENT DOCUMENTS

| | | | |
|---|---|---|---|
| 6,221,024 B1* | 4/2001 | Miesel | A61B 5/0215 600/488 |
| 7,389,134 B1* | 6/2008 | Karicherla | A61B 5/0215 600/375 |
| 8,360,984 B2 | 1/2013 | Yadav et al. | |
| 8,491,518 B2 | 7/2013 | Schnell et al. | |
| 2003/0097073 A1* | 5/2003 | Bullister | A61B 5/0031 600/486 |
| 2009/0270740 A1* | 10/2009 | Keilman | A61B 5/0215 600/486 |
| 2011/0066046 A1* | 3/2011 | Young | A61B 5/02241 600/486 |
| 2015/0133796 A1 | 5/2015 | Yadav | |
| 2015/0289772 A1 | 10/2015 | Huang et al. | |
| 2017/0347893 A1* | 12/2017 | Osoegawa | A61B 5/02233 |
| 2021/0378524 A1* | 12/2021 | Verkaik | A61B 5/6876 |

\* cited by examiner

EXTRAVASCULAR CUFF

CROSS-REFERENCE TO RELATED APPLICATION

This application is related to and claims priority to U.S. Provisional Patent Application Ser. No. 62/678,777, filed May 31, 2018, entitled "EXTRAVASCULAR CUFF", and is also related to and claims priority to U.S. Provisional Patent Application Ser. No. 62/750,956, filed Oct. 26, 2018, entitled "EXTRAVASCULAR CUFF", the entire contents of both of which are hereby incorporated herein by reference.

STATEMENT REGARDING FEDERALLY SPONSORED RESEARCH OR DEVELOPMENT n/a

FIELD

The present application relates generally to blood pressure sensors, and, more particularly, to an implantable extravascular blood pressure system, an implantable extravascular cuff, and attachment element adapted to couple the cuff to a blood vessel.

BACKGROUND

A patient's vital signs provide information useful for detecting and/or monitoring medical conditions. Known devices for measuring vital signs include, for example, blood pressure cuffs which attach to a patient's upper arm, pulse oximeters designed to be placed around the patient's fingertip, thermometers for measuring body temperature, stethoscopes for observing biological sounds, and tonometers designed to measure pressure. Although often used to measure pressure inside of an eye, tonometers may also be implanted within a patient to measure blood pressure in the arteries and veins. One or more existing tonometers use a discrete force sensing element known to severely deform the blood vessel during applanation, i.e., flattening caused by the application of pressure. Other types of pressure sensors may be implanted within a blood vessel wall. However, such pressure sensors typically necessitate the presence of significant hardware inside the blood vessel that may be hazardous for the patient including blood flow obstructions and the potential for thrombus formation. Thus, an extravascular pressure sensor that does not breach the vessel wall has fewer safety risks as compared to a more-invasive extravascular tonometer.

The concept of applanation, as it relates to the blood vessel under Laplace's law, dictates that when a pressure sensor causes a blood vessel wall to applanate, the pressure measured inside the pressure sensor will be approximately equal to the pressure measured inside the blood vessel. Contact pressure value generated by applanation depends on the position and level of flattening. However, rigid tonometers performing applanation may generate internal blood vessel wall stress that may compromise the vessel over time and cause measurement errors. Under high stress conditions the tissue may remodel and become thinner in constrained low stress areas and thicker in areas of higher stress where acute bending is imposed on the vessel in regions of high curvature. In addition, rigid tonometers may be prone to errors associated with the size, shape, and position of the tonometer's pressure sensor with respect to the blood vessel on account of not having a means to allow the vessel to expand to facilitate dilation or a pulsatile pressure load.

SUMMARY

The present application provides for an implantable extravascular pressure sensing system including a cuff having a first brace portion, a second brace portion, and a plurality of biasing members movably coupling the first brace portion and the second brace portion to each other. The first brace portion defines a fluid chamber and the fluid chamber defines a recessed aperture. The system also includes a flexible diaphragm coupled to the fluid chamber and sealing the recessed aperture, a fluid disposed within the fluid chamber for exhibiting a hydraulic pressure in communication with the flexible diaphragm, and a pressure sensor coupled to the first brace portion, the pressure sensor being configured to measure a change in the hydraulic pressure when a force is imparted on the flexible diaphragm.

In another aspect of the invention, the flexible diaphragm includes a body having a surface defining an exterior wall of the first brace portion and a skirt surrounding the body.

In another aspect of the invention, the flexible diaphragm is made of a polyurethane material and includes a planar surface adapted to communicate with a flattened portion of a blood vessel wall.

In another aspect of the invention, the fluid disposed within the fluid chamber is a silicone fluid.

In another aspect of the invention, the pressure sensor is a MEMS sensor.

In another aspect of the invention, the system may further comprise an electronic circuit disposed between the flexible diaphragm and the fluid chamber, the electronic circuit defining a first aperture therethrough.

In another aspect of the invention, the system may further comprise a sealing member adjacent the flexible diaphragm, the electronic circuit defining a second aperture therethrough in communication with the first aperture.

In another aspect of the invention, the first brace portion includes a sidewall defining a plurality of ports in fluid communication with the fluid chamber.

In another aspect of the invention, the first brace portion defines a blood vessel securing region at least partially surrounding the flexible diaphragm.

In another configuration, the present application includes an implantable extravascular pressure sensing cuff for attachment around a blood vessel, the cuff including a first brace portion, a second brace portion opposite the first brace portion, and a biasing member coupling the first brace portion to the second brace portion. The first brace portion and the second brace portion each include an abutment structure defining a blood vessel securing region, the blood vessel securing region including a centralized region having a first side, a second side, and a planar surface therebetween, a transition region having an oblong shape adjacent the centralized region, and a cylindrical support surface adjacent the transition region.

In another aspect of the invention, the first brace portion and the second brace portion each include a rigid housing, the rigid housing having a main body including a proximal region and a distal region opposite the proximal region, the proximal region and the distal region defining a housing axis extending therethrough, and the proximal region of the first brace portion having an electronic feedthrough assembly coupled thereto.

In another aspect of the invention, the abutment structure extends from the main body of the rigid housing in a direction transverse to the housing axis.

In another aspect of the invention, the first brace portion includes a plurality of protrusions extending parallel to housing axis, and the biasing member defines a plurality of apertures sized to receive the plurality of protrusions therein.

In another aspect of the invention, the system further comprises a retaining plate overlying the plurality of apertures of the biasing member.

In another aspect of the invention, the system further comprises a second biasing member opposite the biasing member, the second biasing member coupled the first brace portion and the second brace portion to each other.

In another aspect of the invention, the biasing member and the second biasing member are made of a shape memory material and are configured to translate the first brace portion and the second brace portion with respect to each other in response to a force applied to at least one of a group consisting of the first brace portion and the second brace portion by the blood vessel.

In another aspect of the invention, the biasing member includes a pair of opposing ends coupling the first brace portion and the second brace portion to each other, and a plurality of folds disposed between the pair of opposing ends.

In another aspect of the invention, the system further comprises a casing coupled to at least one of a group consisting of the first brace portion and the second brace portion and surrounding the plurality of folds of the biasing member.

In another aspect of the invention, the biasing member defines a plurality of apertures extending along the plurality of folds.

In another aspect of the invention, the blood vessel securing region includes a plurality of rounded edges defining a perimeter around the abutment structure, and the cylindrical support surface is disposed between the rounded edges.

BRIEF DESCRIPTION OF THE DRAWINGS

A more complete understanding of the present application, and the attendant advantages and features thereof, will be more readily understood by reference to the following detailed description when considered in conjunction with the accompanying drawings wherein.

DETAILED DESCRIPTION

Figure 1:
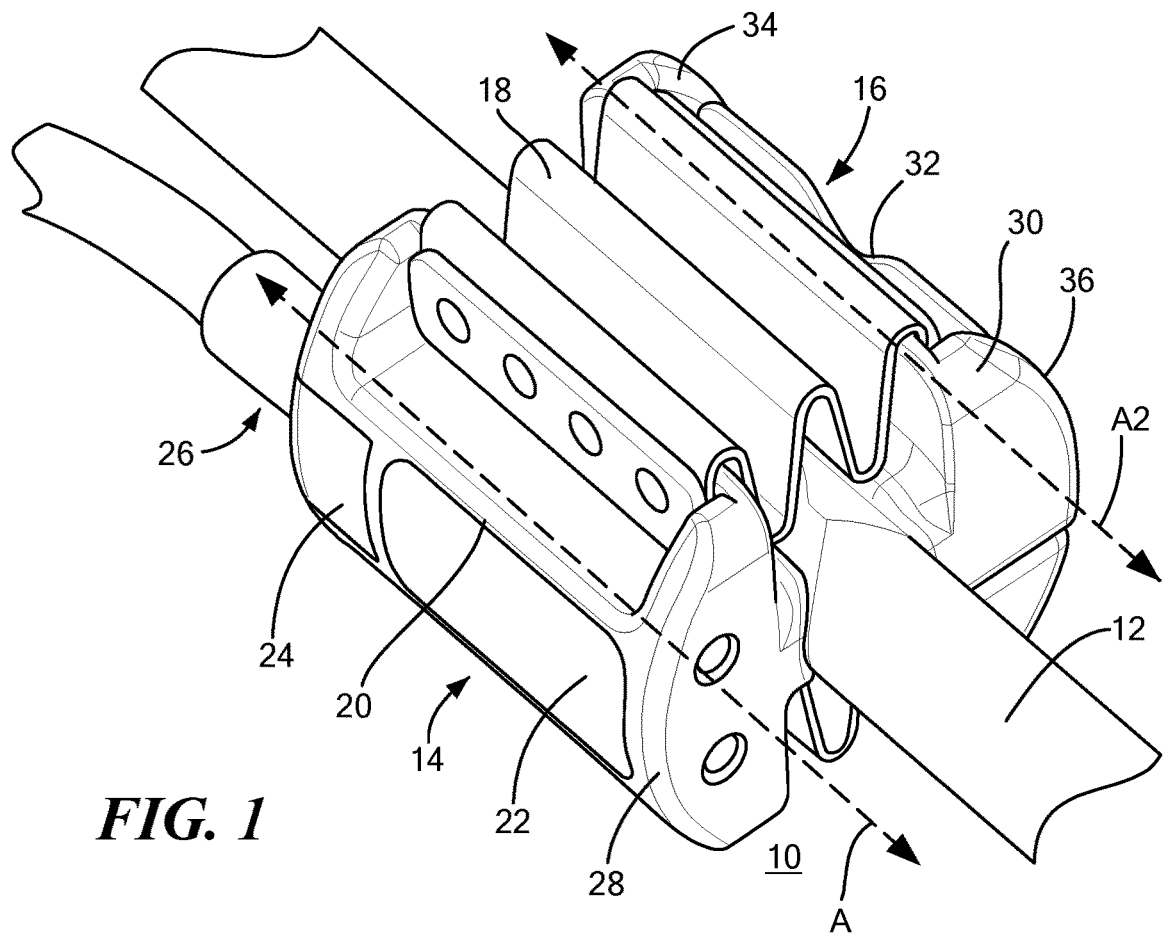
FIG. 1 is a front perspective of an implantable extravascular cuff in accordance with the present disclosure.

Before describing in detail exemplary embodiments, it is noted that the configurations reside primarily in combinations of device and apparatus components related to an implantable extravascular blood pressure sensor, cuff, and attachment element. Accordingly, the device and apparatus components have been represented where appropriate by conventional symbols in the drawings, showing only those specific details that are pertinent to understanding the configurations of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Referring now to the drawings in which like reference designators refer to like elements there is shown in FIG. 1 an exemplary implantable extravascular cuff for a blood vessel generally designated as "10." The implantable extravascular cuff may be referred to herein as a brace or "the cuff 10" and is configured to be implanted within a patient, such as a human or animal patient. Upon implantation, the cuff 10 at least partially surrounds a blood vessel 12, without breaching or significantly obstructing the blood vessel 12, to measure blood pressure and/or perform additional or alternative medical diagnostics. The cuff 10 may surround select portions of the blood vessel 12 without necessitating the complete encircling of the blood vessel 12 or the cuff 10 may surround at least a portion of the blood vessel 12.

In one configuration, the cuff 10 includes a first brace portion 14, a second brace portion 16 opposite the first brace portion 14, and a biasing member 18 coupling the first brace portion 14 to the second brace portion 16. The first brace portion 14 may include a rigid housing 20 having a main body 22 including a proximal region 24 configured to receive an electronic communication assembly 26 and a distal region 28 opposite the proximal region 24, the proximal region 24 and the distal region 28 defining a housing axis "A" extending therethrough. Similarly, the second brace portion 16 may include a rigid housing 20 having a main body 32 including a proximal region 34 and a distal region 36 opposite the proximal region 34, the proximal region 34 and the distal region 36 defining a housing axis "A2" extending therethrough. In one configuration, the first brace portion 14 may house various electronics, such as a pressure sensor, whereas the second brace portion 16 may serve as an attachment element or lock to secure the cuff 10 to the blood vessel 12. In other configurations, the first brace portion 14 and/or the second brace portion 16 may house various medical diagnostic components.

The housing 20 of the first brace portion 14 and the housing 30 of the second brace portion 16 may be made of a titanium material or another biocompatible material having a low density, relatively high strength, and relatively high level of corrosion resistance. The biasing member 18 may be a spring, coil, or the like, made of a shape memory material, such as nitinol, or another stable and fatigue resistant material exhibiting a sufficiently low spring rate to bias the first and second brace portions 14 and 16 a nominal distance from each other when coupled to the blood vessel 12 and to translate with respect to each other in accordance with and/or in response to a force applied to the first and/or the second brace portion 14, 16 by the blood vessel 12 in relation to a size and/or a pressure of the blood vessel 12. In other words, the biasing member 18 acts as a spring to provide suspension and vary the distance between the first brace portion 14 and the second brace portion 16 in accordance with the pressure applied thereto by the blood vessel 12. The biasing member 18 is configured to assist the cuff 10 in accommodating blood vessels of varying size and adjust for dilation and constriction of the blood vessel 12 while maintaining mechanical coupling of an outer surface of a diaphragm with a wall of the blood vessel 12 in applanation when the cuff 10 is used as a blood pressure sensor.

Figure 2:
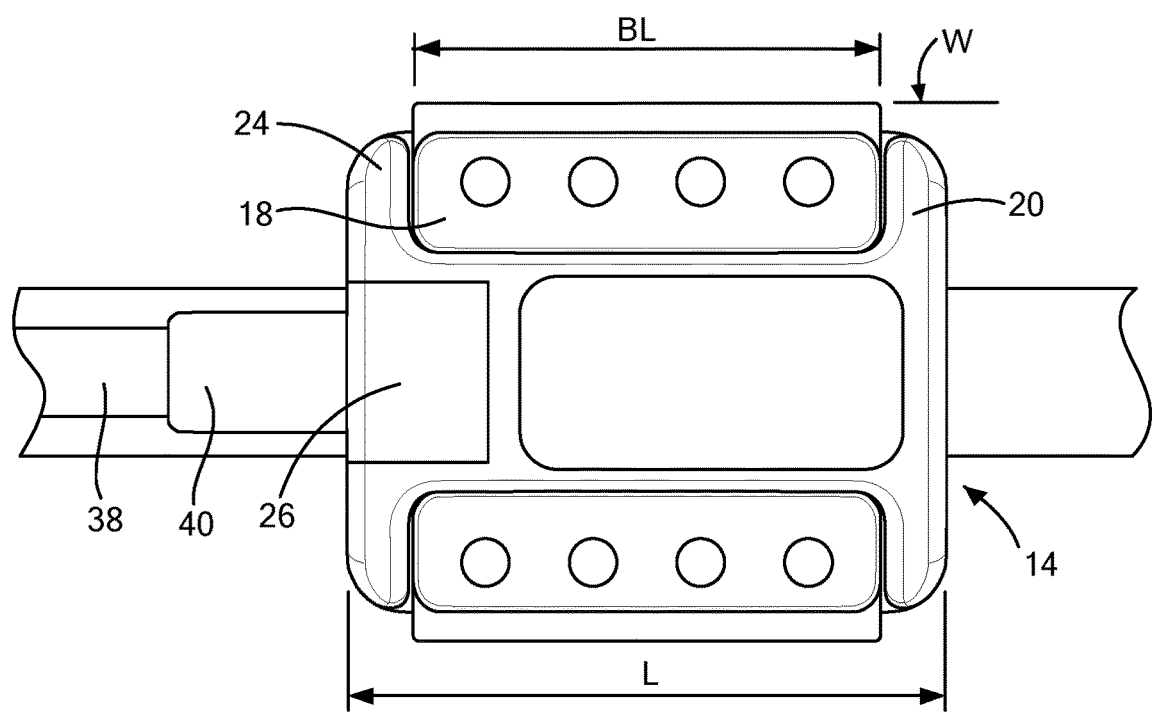
FIG. 2 is a side view of the cuff shown in FIG. 1.

Referring now to FIG. 2, the housing 20 of the first brace portion 14 may include a length "L" between 8.0 to 12.0 millimeters ("mm"), for example 10.0 mm, and a width "W" between 7.0 to 11.00 mm, for example 9.0 mm. In addition, the biasing member 18 may include a length "BL" between 6.00 mm to 9.00 mm, such as 7.80 mm. The housing 30 of the second brace portion 16 may have the same or similar dimensions as those described with respect to the housing 20 of the first brace portion 14. The dimensions described herein are provided for exemplary purposes as other dimensions are within the scope of the present disclosure. The electronic communication assembly 26, which is configured to couple to the proximal region 24 of the first brace portion 14, may include an electric cable 38 and a semi-flexible sleeve 40. For example, the electric cable 38 may be flexible and may include a covering surrounding one or more electric wires (not shown) extending throughout the covering which establish communication between electronics that may be disposed within the first brace portion 14 and at least one of a power source, a controller, and a processor (not shown) external to or implanted within the patient. The electric cable 38 may have a diameter between 0.5 to 1.5 mm, such as 1.0 mm. The sleeve 40 surrounds a portion of the electric cable 38 at an interface between the proximal region 24 of the housing 20 and the electric cable 38. The sleeve 40 provides bend relief for the electric cable 38 to prevent unwanted stress while maintaining flexibility. As such, the sleeve 40 may be solvent bonded to the outer surface of electric cable 38 with the sleeve 40 being optionally interlocked in epoxy when coupling to the housing 20. The sleeve 40 may be made of a material such as, without limitation, polyurethane, and may include a length between 2.0 mm to 4.0 mm, such as 3.0 mm, and a diameter between 1.5 mm to 2.5 mm, such as 2.0 mm.

Figure 3:
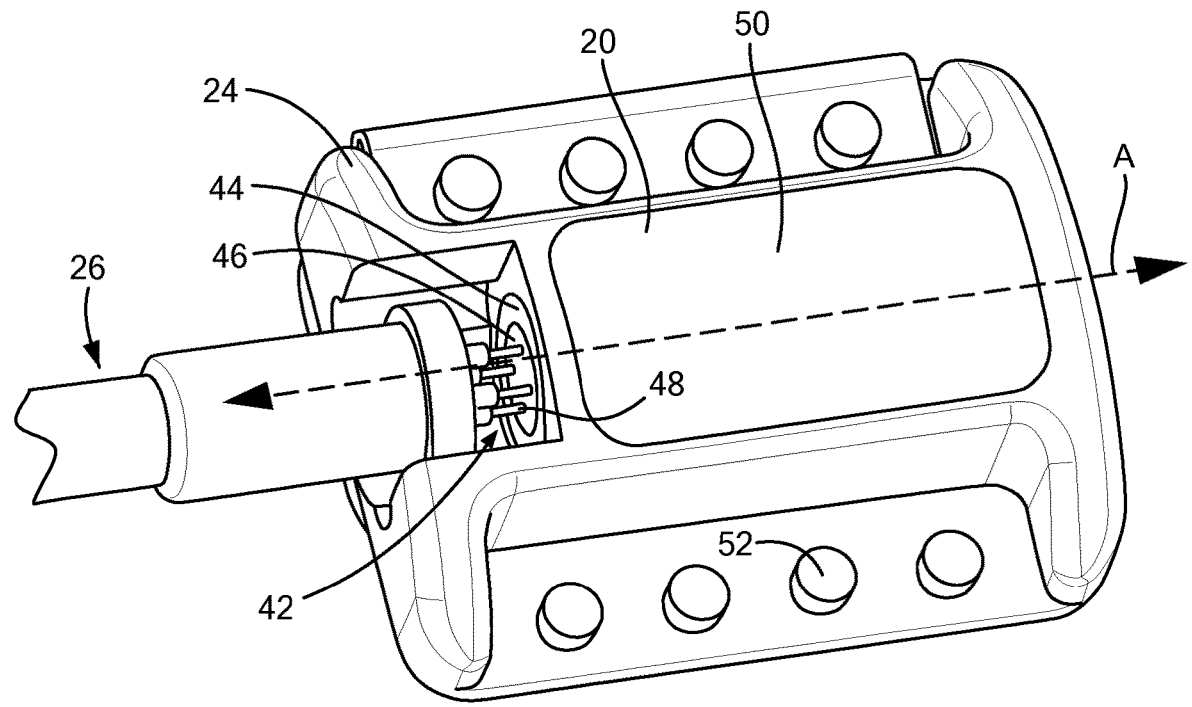
FIG. 3 is a side perspective view of the cuff shown in FIG. 1 showing an electronic feedthrough assembly disconnected from the cuff.

Referring now to FIG. 3, the proximal region 24 of the housing 20 may include an electronic feedthrough assembly 42 coupled thereto for providing a leak-tight passage of electrical conductors to the electronic communication assembly 26. For example, the electronic feedthrough assembly 42 may include a flange 44 laser welded to the housing 20, an insulator 46, e.g., a ceramic insulator, coupled to the flange 44, and one or more wires 48 extending through the flange 44 for coupling to the wires of the electric cable 38. A cover 50 is coupled to the housing 20 to cover the wires 48 and electronics within the housing 20. In one configuration, the cover 50 is made from the same material as the housing 20, such as titanium, for providing a leak-tight enclosure. The cover 50 may also be made from an alternative material that is biocompatible and otherwise suitable for implantation, as is known to a person of ordinary skill in the art of implantable devices.

Figure 4:
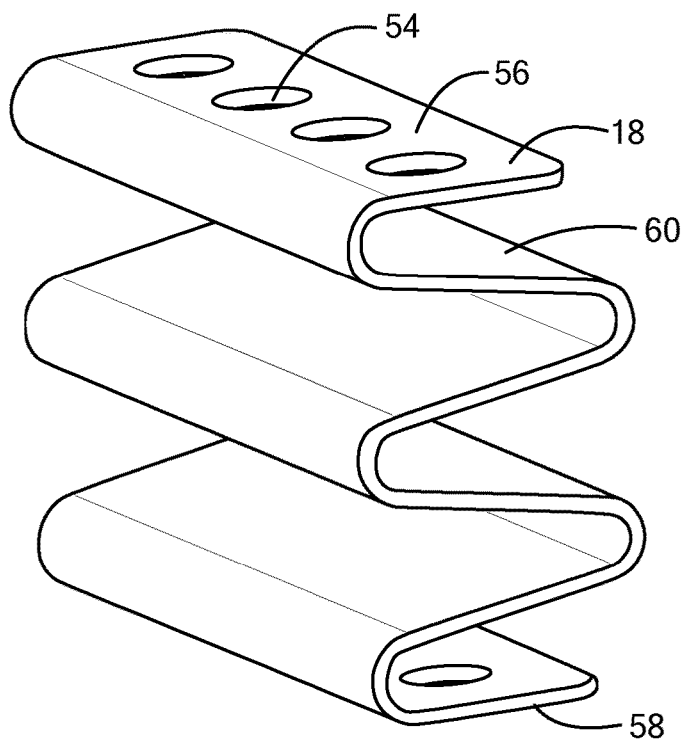
FIG. 4 is a side perspective view of a biasing member of the cuff shown in FIG. 1.

In one configuration, the first brace portion 14 includes one or more protrusions 52 extending parallel to housing axis A and, as shown in FIG. 4, the biasing member 18 defines one or more apertures 54 sized to receive the protrusions 52 through the apertures 54 to couple the biasing member 18 to the housing 20. The biasing member 18 may include a pair of opposing ends 56 and 58 having one or more curved folds 60 therebetween. The folds 60 may be produced in various thicknesses to produce different spring rates. For example, the biasing member 18 may be laser cut to produce the folds 60 having a select thickness and a relatively planar surface. Finishing processes may be applied during manufacturing to form the folds 60 into shape, for example, to exhibit corrugations, and to provide rounded edges for making the biasing member 18 relatively less sharp and less-traumatic to surrounding tissue than that which would occur with relatively straight edges as incidental contact may occur during the implant procedure.

Figure 5:
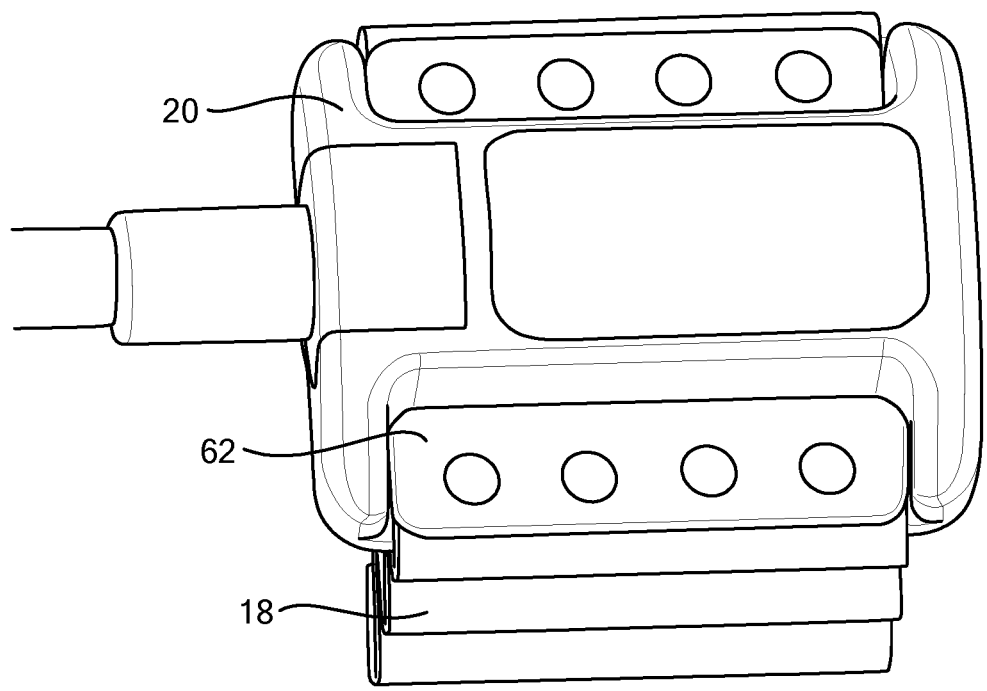
FIG. 5 is a top perspective view of the cuff shown in FIG. 1 showing the biasing member of FIG. 4 coupled to cuff.
Figure 6:
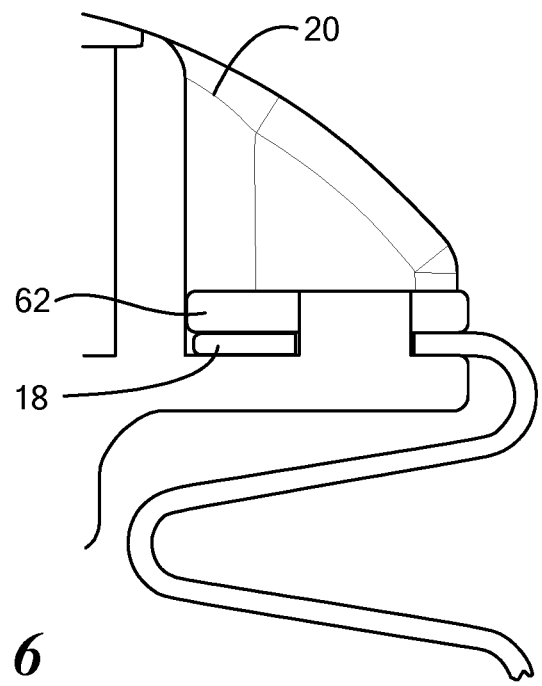
FIG. 6 is a zoomed in front view of the cuff shown in FIG. 5.

Referring now to FIGS. 5 and 6, the biasing member 18 is shown coupled to the housing 20 with a retaining plate 62 overlying the biasing member 18 that may be laser welded to the housing 20 to prevent the biasing member 18 from pivoting transversely with respect to the housing axis (FIG. 1).

Figure 7:
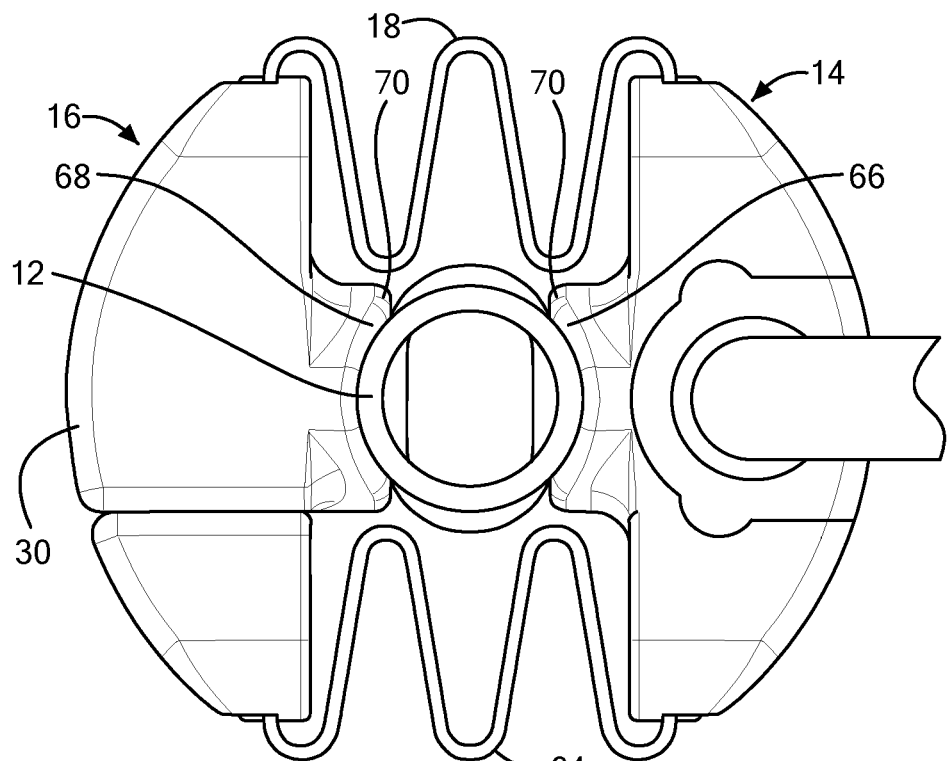
FIG. 7 is a rear view of the cuff shown in FIG. 1.

Referring now to FIG. 7, a rear view of the cuff 10 is provided showing the biasing member 18 and a second biasing member 64 movably coupling the first brace portion 14 and the second brace portion 16 of the cuff 10 to each other. As such, the housing 30 of the second brace portion 16 may include one or more protrusions similar to the protrusions 52 of the first brace portion 14 to provide a connection in the manner described with respect to the first brace portion 14. In addition, the second biasing member 64 may include the properties described above with respect to the biasing member 18. For example, the second biasing member 64 allows the first brace portion 14 and the second brace portion 16 to move or translate with respect to each other to provide the suspension system together with the biasing member 18. In one or more configurations, the first biasing member 18 and the second biasing member 64 may move in unison and may have a similar or the same size, shape, and spring constant with respect to each other to maintain alignment of the housings 20 and 30 with an axis of the blood vessel to facilitate movement of the housings 20 and 30 toward and away from each other with changes in a diameter of the blood vessel 12 and minimize misalignment due to rotational or side-to-side movement. Further, the respective locations of the biasing member 18 and the second biasing member 64 may be interchangeable.

The biasing member 18 and the second biasing member 64 allow an abutment structure 66, i.e., inner wall, of the first brace portion 14 and an abutment structure 68 of the second brace portion 16 to move with respect to each other when at least partially surrounding the blood vessel 12. In particular, the abutment structures 66 and 68 each define a blood vessel securing region 70 sized and shaped to receive the blood vessel 12 therein. The abutment structure 68 of the second brace portion 16 may include the same or similar features.

Figure 8:
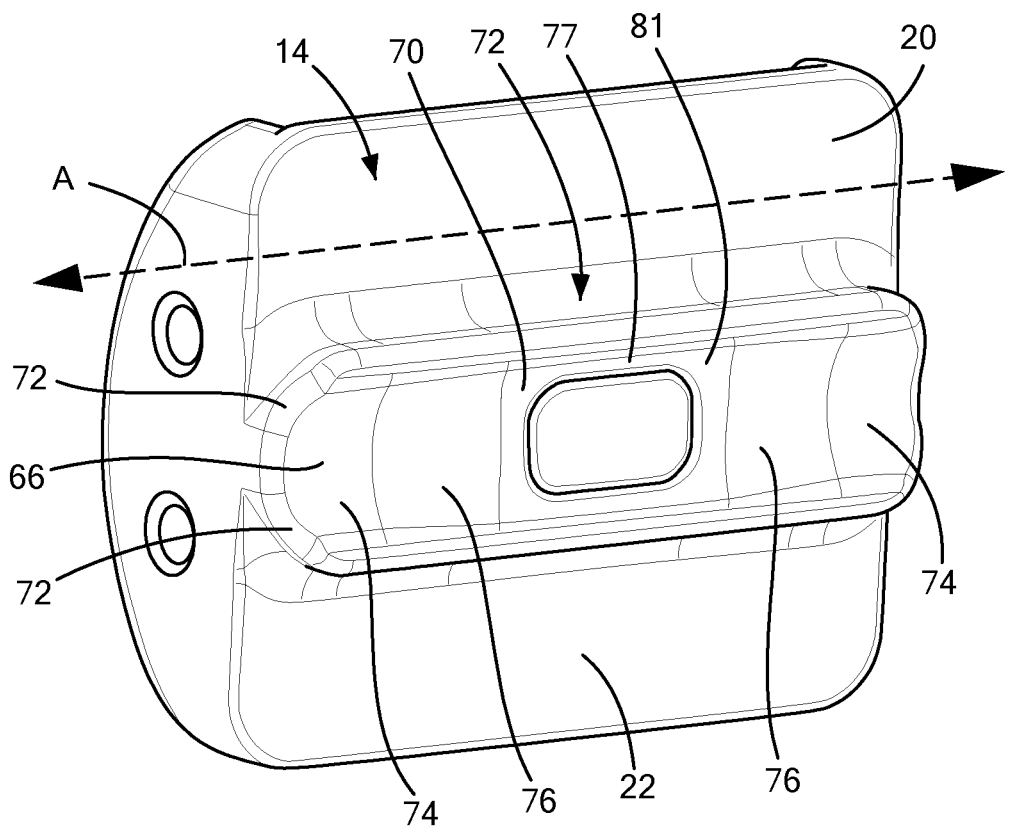
FIG. 8 is an inside view of a blood vessel securing region of the cuff shown in FIG. 1.

Referring now to FIG. 8, the blood vessel securing region 70 includes one or more curved regions, such as a pair of curved or rounded edges 72, one or more cylindrical support surfaces 74, and one or more transition regions 76 adapted for contact with the blood vessel wall. The securing region 70 may have sufficient depth and curvature to maintain long-term alignment of the housing axis with an axis of the blood vessel 12 to prevent misalignment due to rotational movement and/or forces that would cause the sensor tilt or displace in a direction perpendicular to the artery axis. The rounded edges 72 define a perimeter around the abutment structure 66. The cylindrical support surface 74 is disposed between the rounded edges 72 at one or both ends of the abutment structure 66 along the axis A. The transition regions 76 extend between the cylindrical support surfaces 74 and a centralized region 77 that is relatively flat or planar. In other words, the centralized region 77 may include a first side 79 and a second side 81 each having the transition region 76 adjacent thereto with the cylindrical support surface 74 adjacent the transition region 76. The transition regions 76 exhibit a relatively obround shape in contrast to the relatively circular shape of the cylindrical support surface 74. In other words, the transition region 76 exhibits a concave geometry with respect to the centralized region 77 and the abutment structure 66. The planar surface of the centralized region 77 is configured to communicate with a flattened portion of a blood vessel wall.

When the cuff 10 is used as a blood pressure sensor, the transitional geometry exhibited by the transition regions 76 is adapted to minimize stress imposed on the blood vessel 12 in undergoing a forced transition from a circular geometry to a constrained flattening of the blood vessel for achieving applanation and accurate blood pressure transduction through the blood vessel wall to a diaphragm, as explained in further detail below. The design of the abutment structure 66 allows the cuff 10 to least partially surround the blood vessel 12 without overly constraining the blood vessel 12 when obtaining the blood pressure measurements or performing alternative medical diagnostics.

Figure 9:
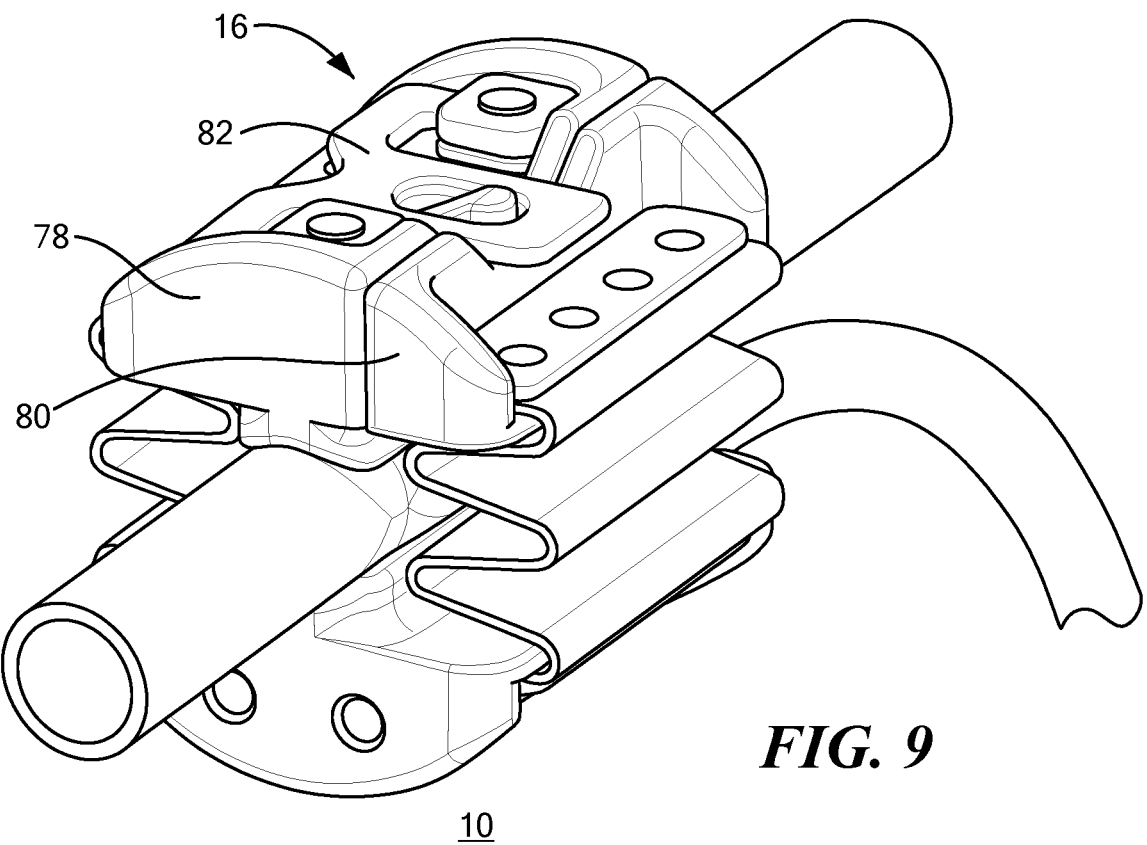
FIG. 9 is another perspective view of the cuff shown in FIG. 1.
Figure 10:
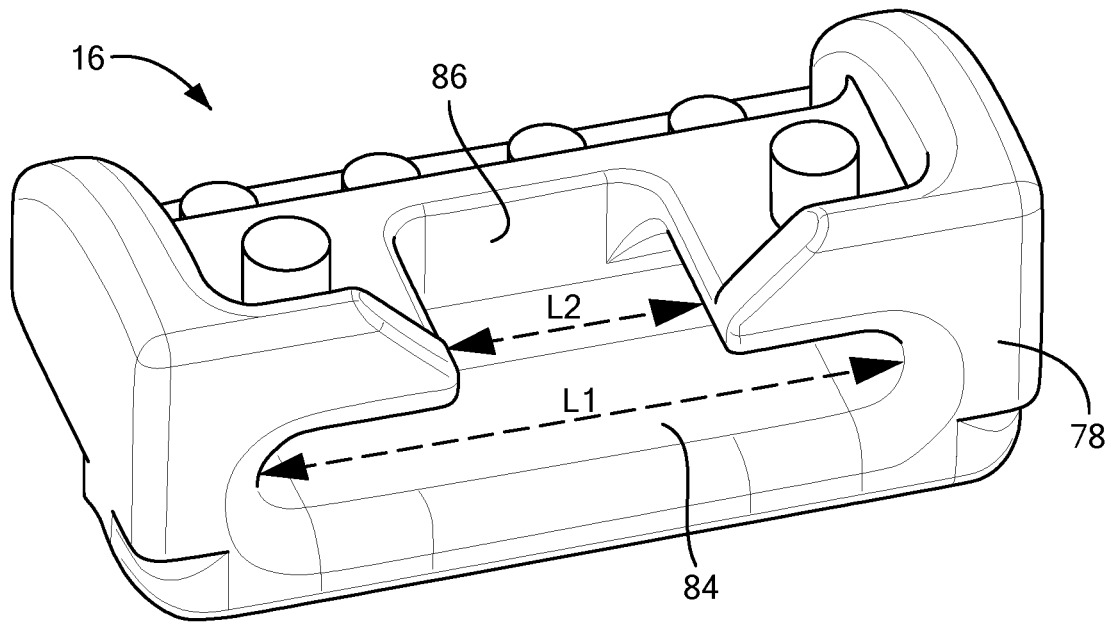
FIG. 10 an inside view of a female body of an attachment element associated with a brace portion of the cuff shown in FIG. 1.
Figure 11:
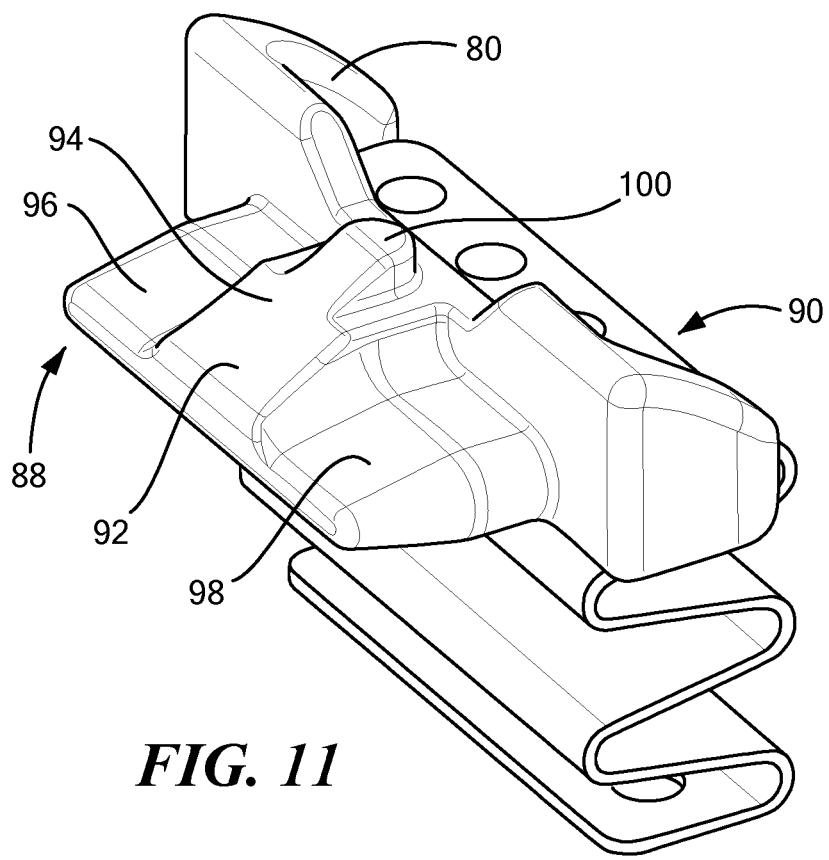
FIG. 11 is an inside view of a male body of the brace portion shown in FIG. 10.

Referring now to FIG. 9, a perspective view of the cuff 10 is provided depicting the second brace portion 16 functioning as an attachment element to secure the brace 10 to the blood vessel 12. The second brace portion 16 may include a female body 78, a male body 80, and a retention element 82 configured to assist in coupling the female body 78 and the male body 80 to each other. For example, as shown in FIGS. 10 and 11, in order to couple the female body 78 (FIG. 10) and the male body 80 (FIG. 11) to each other, the female body 78 defines a first slot 84 and a second slot 86 proximate the first slot 84, the first slot 84 having a length "L1" longer than a length of the second slot "L2." The male body 80 includes an insertion member 88 sized to be received within the first slot 84 of the female body 78 and coupling interface 90 for receiving the biasing member 18, the coupling interface 90 extending in a direction away from the insertion member 88.

Figure 12:
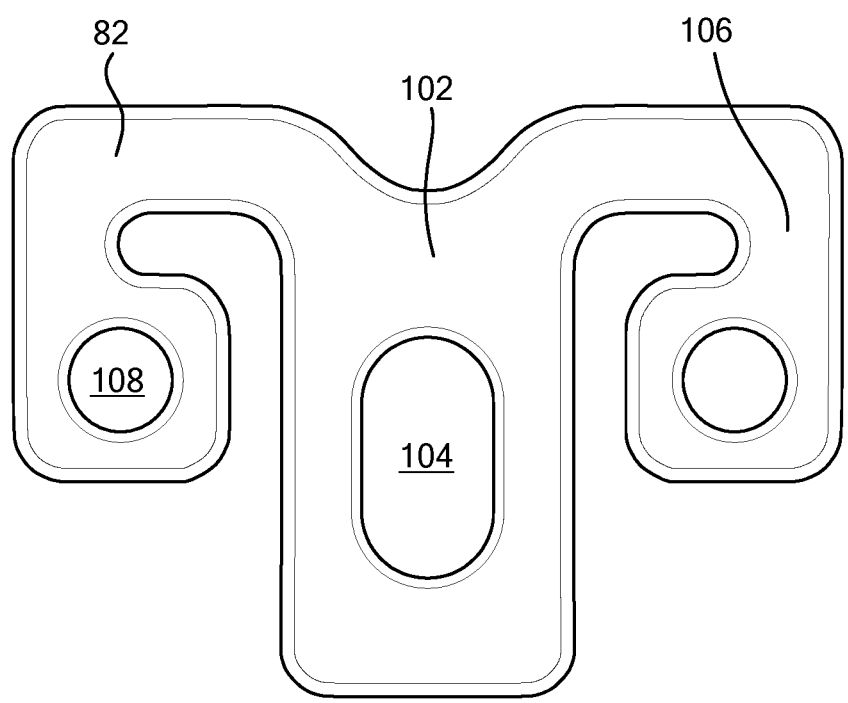
FIG. 12 is a top view of a retention element of the female body shown in FIG. 10.

In one configuration, the insertion member 88 includes a mid-portion 92 defining a sloped region 94, and a pair of outer portions 96 and 98, proximate the mid-portion 92. The pair of outer portions 96 and 98 taper in a direction away from the coupling interface 90 to assist in guiding the insertion member 88 into the first slot 84 of the female body 78. As such, the second brace portion 16 provides a relatively quick and simple process for securing the cuff 10 to the blood vessel 12 that may be useful in circumstances such as surgical implantation of the cuff 10. A latch member 100 protrudes from the sloped region 94 of the insertion member 88 and, as shown in FIG. 12, the retention element 82 includes a base 102 defining an aperture 104 sized to retain the latch member 100 therein when the female body 78 and the male body 80 are coupled to each other. The retention element 82 may be made of a shape memory material, such as nitinol, having a variable thickness chosen based upon a desired stiffness of the retention element 82. Such shape memory material may be flexible to facilitate both latching and unlatching of the female body 78 and the male body 80.

Figure 13:
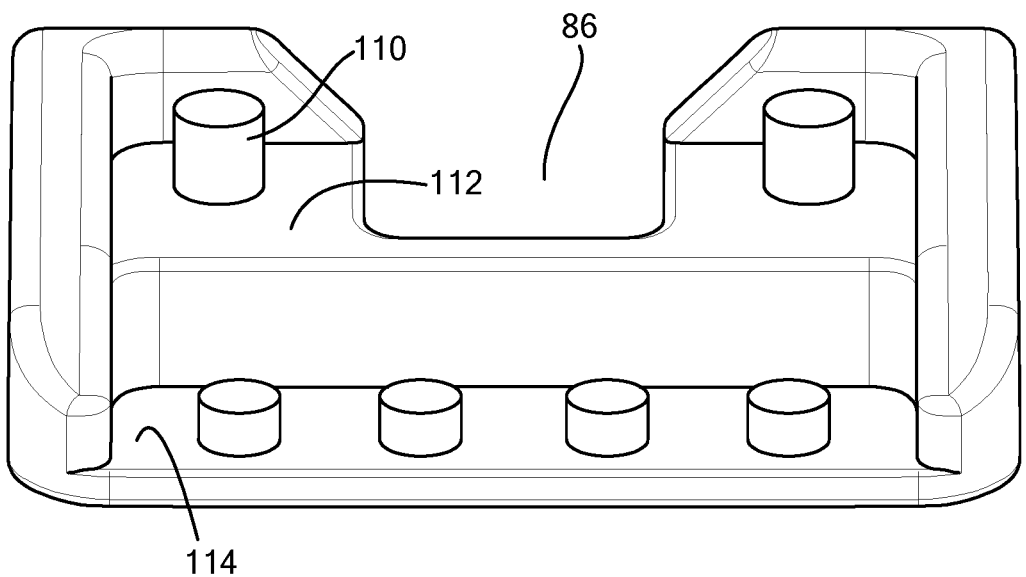
FIG. 13 is a top perspective view of the female body shown in FIG. 10.
Figure 14:
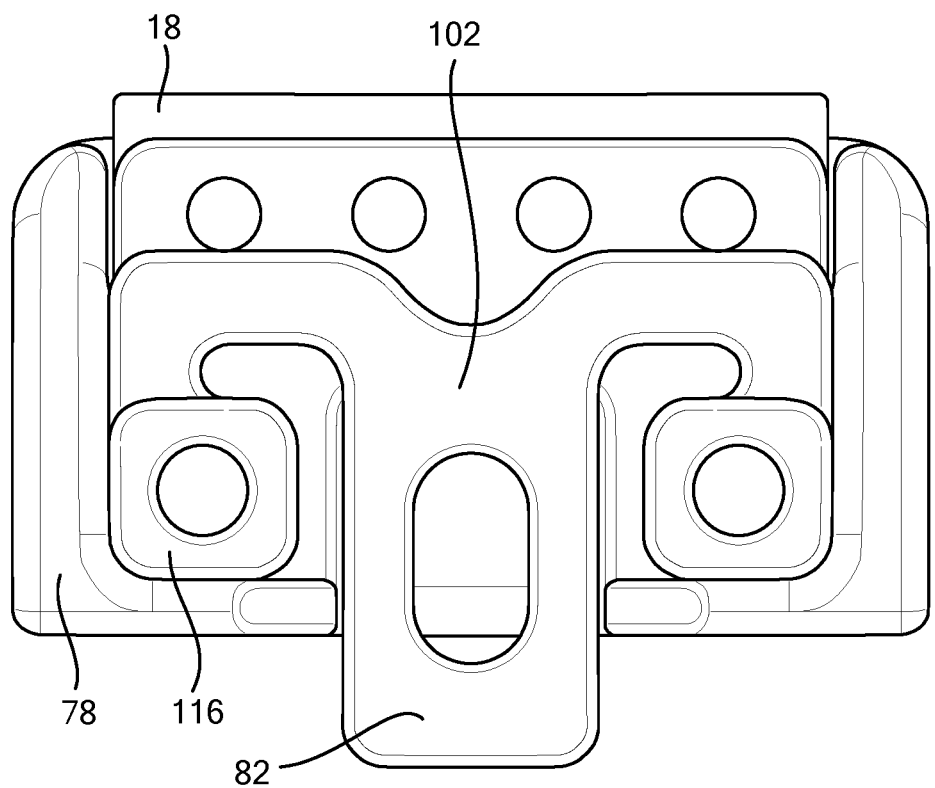
FIG. 14 is a top view of the retention element shown in FIG. 12 coupled to the female body shown in FIG. 10.

Referring now to FIGS. 12-14, the base 102 of the retention element 82 is sized to be inserted within the second slot 86 of the female body 78. One or more retaining arms 106 extend from the base 102 with each retaining arm 106 defining a retention aperture 108. The retention aperture 108 is sized to surround one or more retention members 110 (FIG. 13) extending from a mounting surface 112 of the female body 78. The mounting surface 112 at least partially defines the second slot 86 for receiving the base 102 of the retention element 82 therein. Similar to the coupling interface 90 (FIG. 11), the female body 78 includes a coupling interface 114 for receiving the biasing member 18 of the cuff 10.

Figure 15:
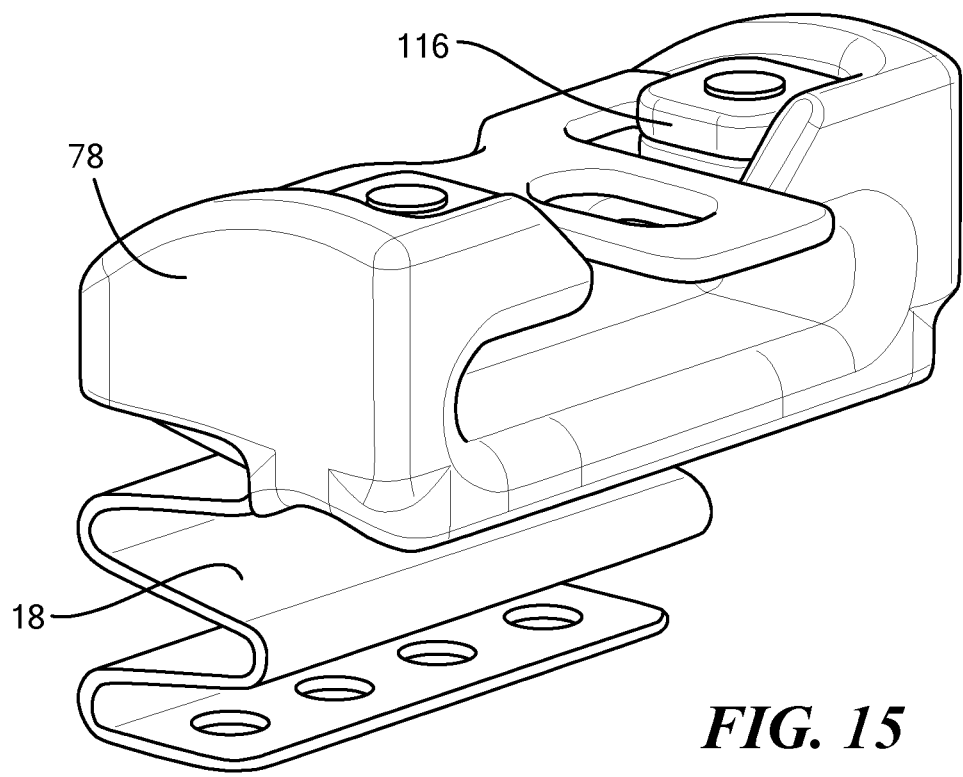
FIG. 15 is a perspective of the female body being coupled to a biasing member shown in FIG. 1.
Figure 16:
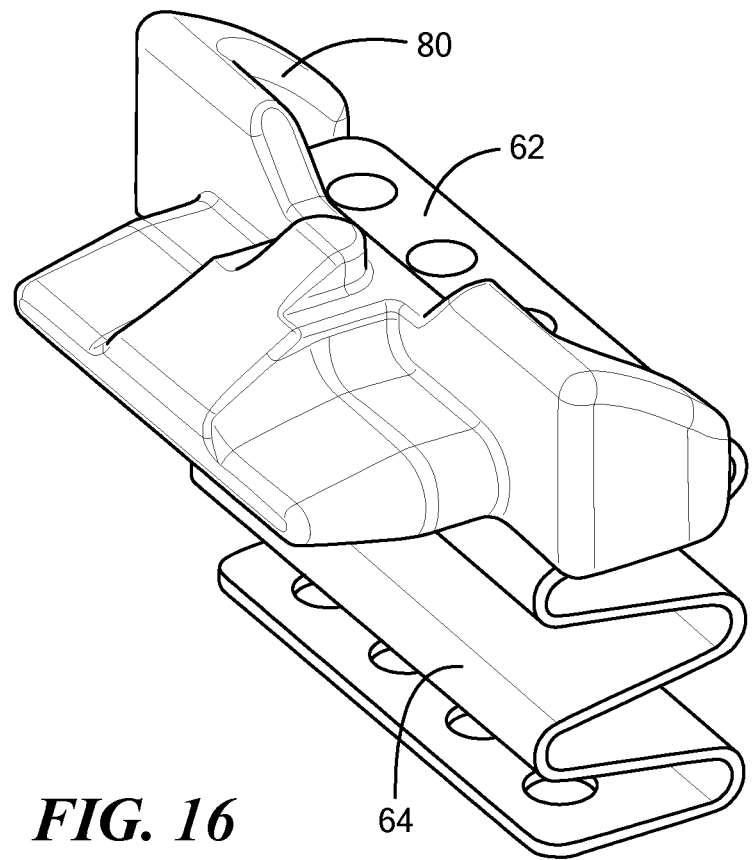
FIG. 16 is a perspective of the male body being coupled to a biasing member shown in FIG. 1.

Referring now to FIGS. 15-16, the biasing member 18 may be coupled to the female body 78 and the second biasing member 64 coupled to the male body 80. One or more retaining rings 116 are sized to constrain a portion of the retention element 82 against the female body 78. The retaining plate 62 may be coupled to the female body 78 in the manner described above with respect to the retaining plate 62 and the male body 80, such as by laser welding. FIG. 16 depicts a perspective view of the male body 80 having the retaining plate 62 coupled thereto adjacent the second biasing member 64.

Figure 17:
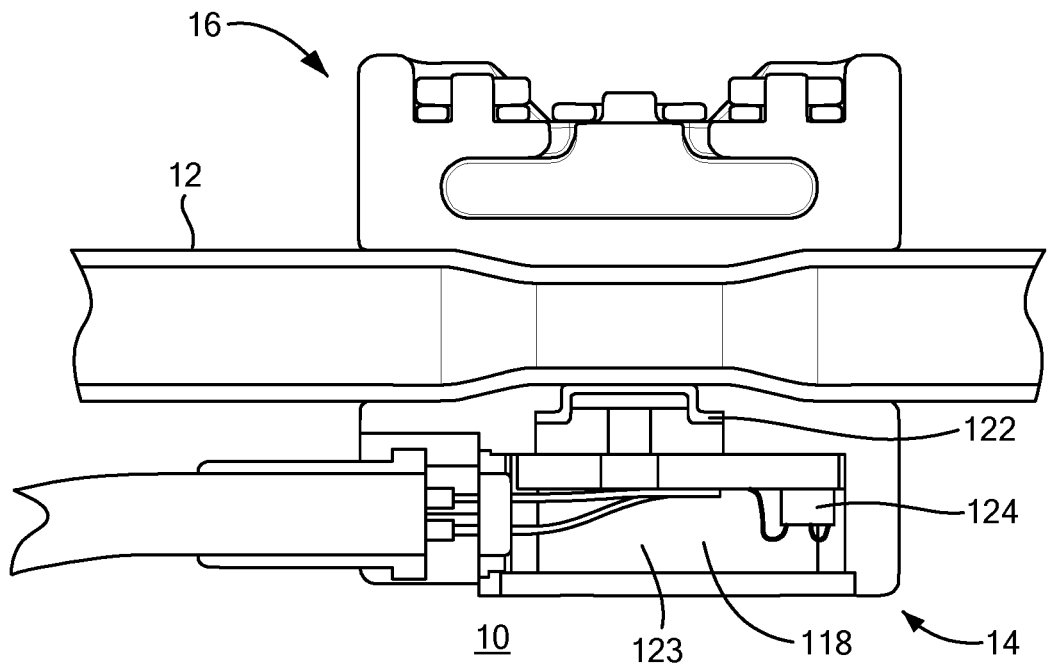
FIG. 17 is a mid-plane section view of the cuff shown in FIG. 1 having an implantable sensor.
Figure 18:
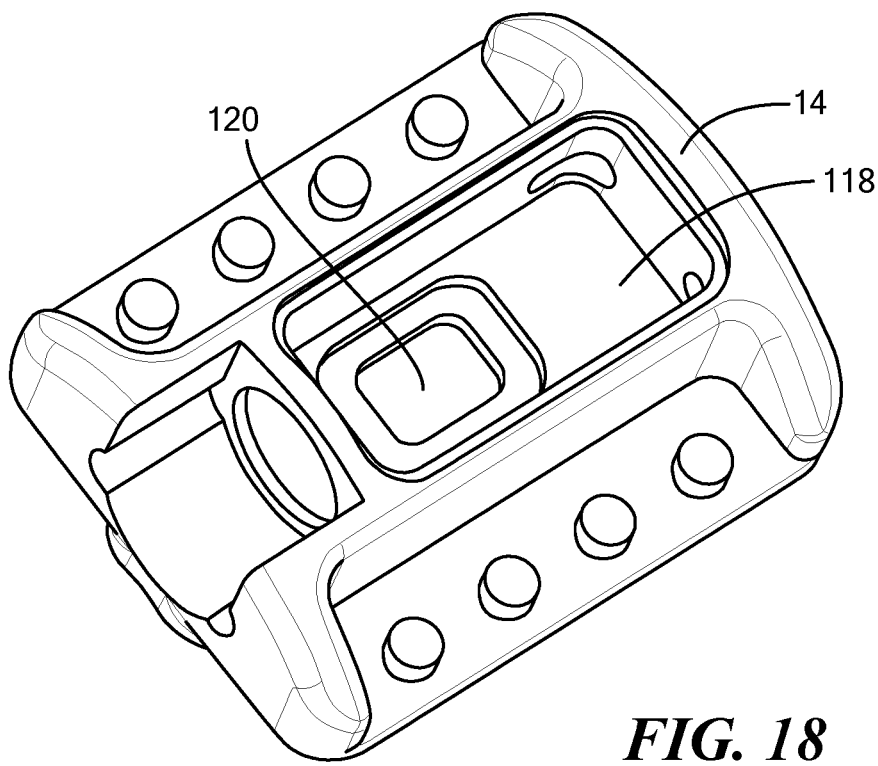
FIG. 18 is an inside view of the sensor shown in FIG. 17 shown a fluid chamber.

Referring now to FIG. 17, a mid-plane section view of the cuff 10 is depicted at least partially surrounding the blood vessel 12 with the first brace portion 14 including an implantable extravascular sensor and the second brace portion 16 being configured as the locking element to secure the cuff 10 to the blood vessel 12. For example, in one configuration, the first brace portion 14 defines a fluid chamber 118 and, as shown in FIG. 18, the fluid chamber 118 defines a recessed aperture 120. A flexible diaphragm 122 is coupled to the fluid chamber 118 which seals the recessed aperture 120. A fluid, generally depicted as numeral 123, such as silicone fluid, may be disposed within the fluid chamber 118 for exhibiting a hydraulic pressure consistent with the pressure applied to the diaphragm 122, such as an inner surface of the diaphragm 122 from the blood vessel 12. Hydraulic generally refers to fluid in a confined space (closed system) wherein the fluid is a medium to transmit force. This is in accordance with the discovery of Pascal that a pressure applied to any part of a confided fluid transmits to every other part with no loss. The pressure acts with equal force on all equal areas of the confining walls in a direction perpendicular to the wall surfaces. A pressure sensor 124 is coupled to the first brace portion 14 and configured to measure a change in the hydraulic pressure when the force is imparted on the diaphragm 122, such as on an outer surface of the diaphragm 122. As such, the diaphragm 122 may be a compliant diaphragm configured to be secured, i.e., mechanically coupled, against a wall of the blood vessel 12 to facilitate transduction of the blood pressure through a wall of the blood vessel 12. The biasing member 18 may be a "spring-like" biasing member 18 configured to couple the first brace portion 14 to the second brace portion 16 to maintain mechanical coupling of the diaphragm 122 with a wall of the blood vessel 12 during vasoconstriction/dilation.

The hydraulic pressure within the diaphragm 122 can be measured by the pressure sensor 124, with the pressure sensor 124 being a resistive or capacitive sensor, for example a MEMS sensor or MEMS pressure die. In one configuration, the pressure sensor 124 may be that which is marketed and sold under the name NovaSensor®. In an alternative configuration, the pressure sensor 124 may be a silicon, micro-machined, piezo resistive pressure sensing chip within the Smi510E Series. In other configurations, the pressure sensor 124 may be another type of sensor configured to measure hydraulic pressure.

Figure 19:
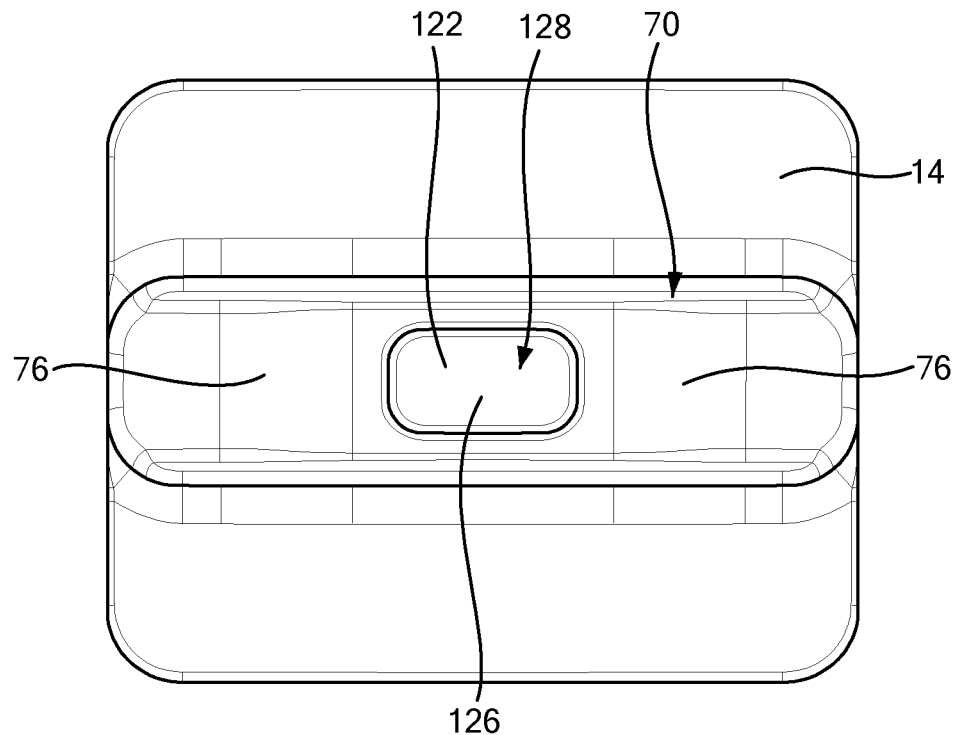
FIG. 19 is side inside view of a brace portion shown in FIG. 1 having a diaphragm.

Referring now to FIG. 19, the diaphragm 122 may be at least partially surrounded by the first brace portion 14, for example, between the transition regions 76 of the blood vessel securing region 70. The relatively large dimensions of the transition regions 76 with respect to the cuff 10 are configured to isolate the diaphragm 122 from external forces and movement of the cuff 10. In addition, the diaphragm 122 may include a body 126 having a surface 128 defining an exterior wall of the first brace portion 14 such that the surface 128 faces the blood vessel 12 when the cuff 10 is coupled thereto. The body 126 may include a length between 2.0 mm to 3.00 mm, for example 2.5 mm, to provide a relatively large surface area in contact with the blood vessel 12 to transmit pressure across the blood vessel wall. An inferior surface of the body 126 may be textured with a porous structure or microneedles to produce a secure mechanical coupling of the brace 10 to tissue of the blood vessel wall to minimize rotational and side-to-side motion artifact.

Figure 20:
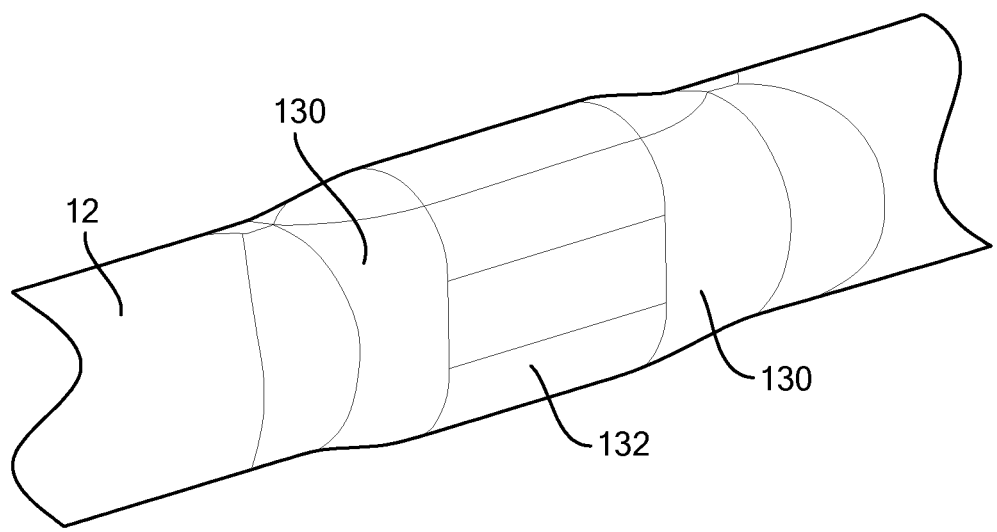
FIG. 20 is a view of the blood vessel with the forces applied by the cuff shown in FIG. 1 and the resulting curvature.
Figure 21:
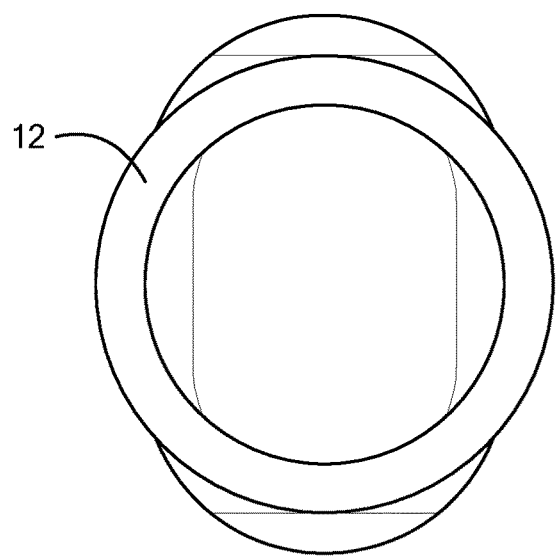
FIG. 21 is a front cross-sectional view of the blood vessel shown in FIG. 20.

Referring now to FIG. 20, the blood vessel 12 is shown with the cuff 10 removed, but the forces from the cuff 10 applied, including two transition sections 130 sized to be received within the transition regions 76 such that the transition regions 76 contour the blood vessel 12 without straining the blood vessel 12. An applanation section 132 of the blood vessel 12 is disposed between the transition sections 130 and is configured to be in contact with the diaphragm 122 to obtain the blood pressure measurements. The transition sections 130 of the blood vessel 12 may include a length between 1.5 mm to 1.8 mm, such as 1.750, whereas the applanation section 132 of the blood vessel 12 may include a length between 3.0 mm to 4.0 mm, such as 3.5 mm. A mid-portion of the applanation section 132 may include a width between 1.0 mm to 1.2 mm, such as 1.1 mm. The blood vessel securing region 70 of the cuff 10 is configured to displace the blood vessel 12, as shown in FIG. 21, from a circular shape to an oblong shape, thus flattening the blood vessel 12 to achieve applanation along the surface area of the diaphragm 122. In order to obtain a sufficient, but not excessive, flattening of the vessel for successfully measuring pressure, the offset of the normally cylindrical blood vessel wall with respect to the applanation section 132 of the blood vessel 12 may be in the range of 18% to 22%, such as 20% applanation.

Figure 22:
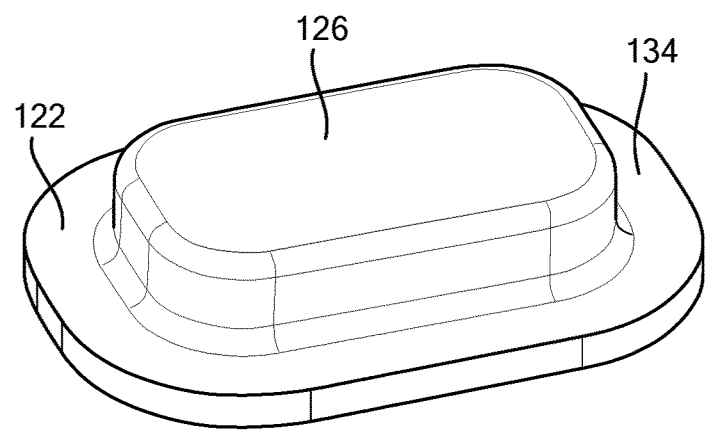
FIG. 22 is perspective view of the diaphragm shown in FIG. 19.

Referring now to FIG. 22, a perspective view of the diaphragm 122 is provided including the body 126 surrounded by a skirt 134. The skirt 134 acts as a flange when the diaphragm 122 is disposed within the recessed aperture 120 of the first brace portion 14. The diaphragm 122 may include a thickness between 50 micrometers ("um") to 200 um, such as 100 um and may be made of a polyurethane material, such as that marketed and sold under the name BioSpan® Segmented Polyurethane. The diaphragm 122 may be manufactured using a dip molding process with the skirt 134 being die cut to form the boundary of skirt 134 upon completion of such process. Alternatively, the diaphragm 122 may be compression or injection molded. The diaphragm 122 may include a planar surface that is adapted to communicate with a flattened portion of the blood vessel 12 wall.

Figure 23:
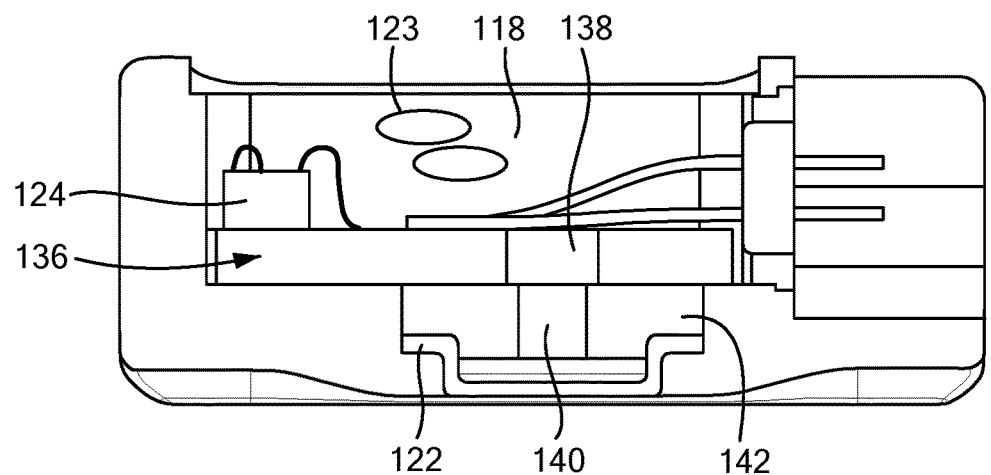
FIG. 23 is inside view of the cuff showing an electronic circuit disposed between the fluid chamber and the sensor.
Figure 24:
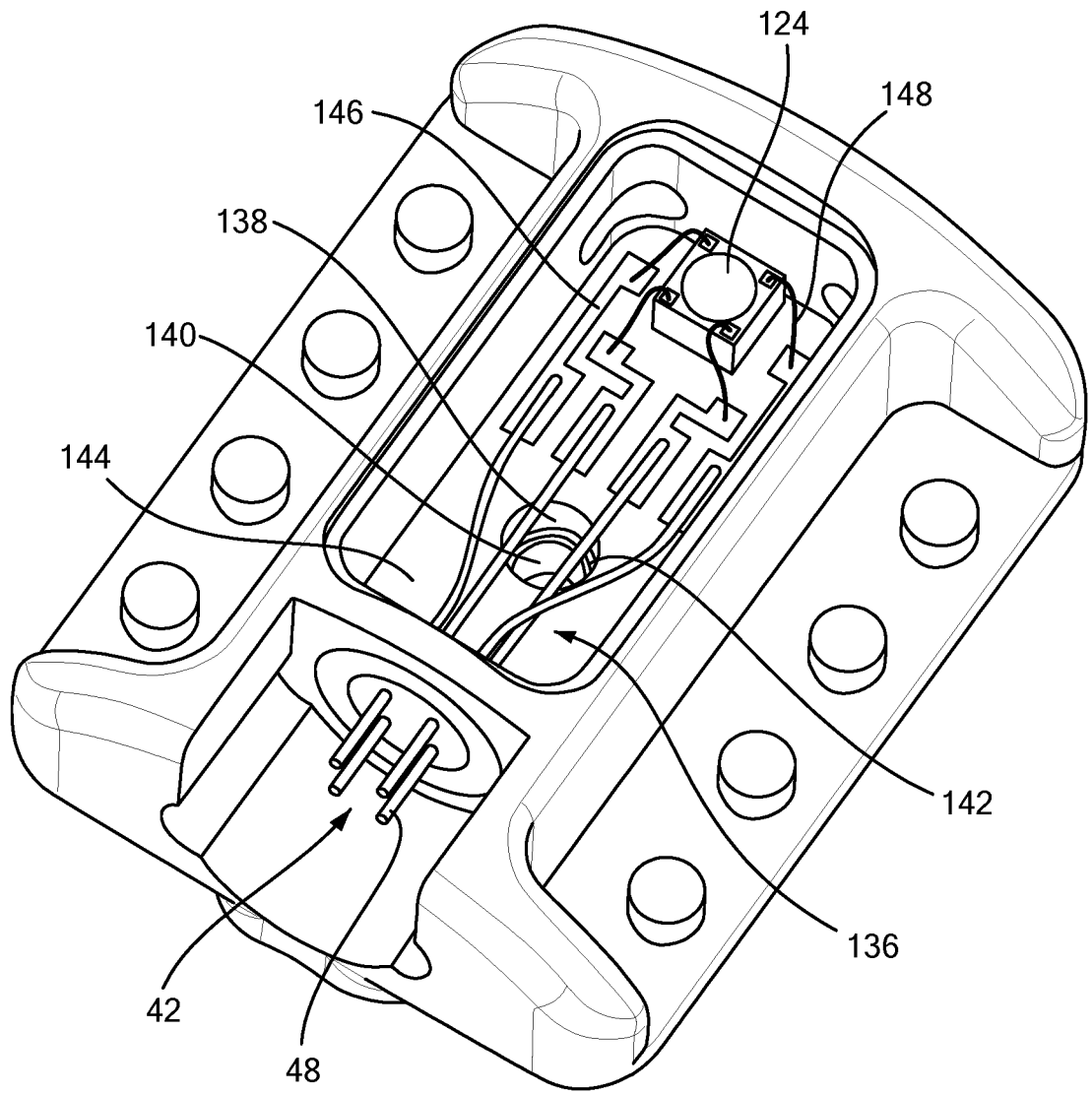
FIG. 24 is another view of the electronic circuit shown in FIG. 23.
Figure 25:
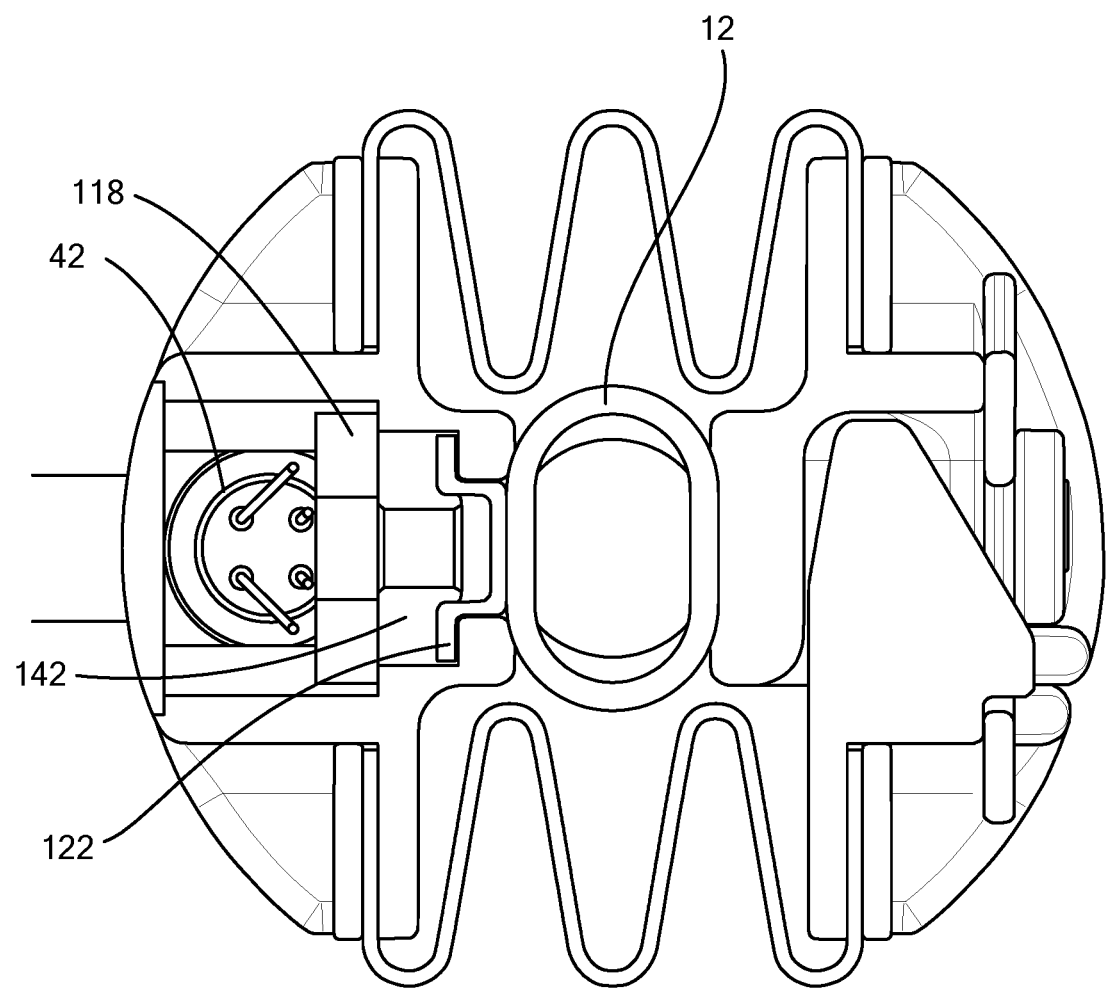
FIG. 25 is a cross-sectional view of the cuff shown in FIG. 1 showing the electronic feedthrough assembly shown in FIG. 3.

Referring now to FIGS. 23 and 24, an electronic circuit 136 is disposed between the diaphragm 122 and the fluid chamber 118, for example adjacent the pressure sensor 124. The electronic circuit 136 may include, but is not limited to, a printed circuit board 144 and one or more solder pads 146 for receiving the wires 48 of the electronic feedthrough assembly 42. In addition, the pressure sensor 124 may include one or more wires 148 coupled to the solder pads 146 for communicating with the electronic circuit 136 and which allow adjustments in the location of the pressure sensor 124 with respect to the fluid chamber 118. In order to allow the fluid to be in fluid communication with the diaphragm 122 and the pressure sensor 124, the electronic circuit 136 defines a first aperture 138 in communication with a second aperture 140 of a sealing member 142 disposed between the electronic circuit 136 and the diaphragm 122. The sealing member 142 may be made of a titanium material or another suitable material for shielding the electronic circuit 136 from the fluid. Information obtained from the pressure sensor 124 can be sent to a processor, controller, or the like through the electronic feedthrough assembly 42 when coupled to the electric cable 38. FIG. 25 provides a cross-sectional view of the cuff 10 including the electronic feedthrough assembly 42, the enclosed fluid chamber 118, the sealing member 142, and the diaphragm 122 in communication with the blood vessel 12.

Figure 26:
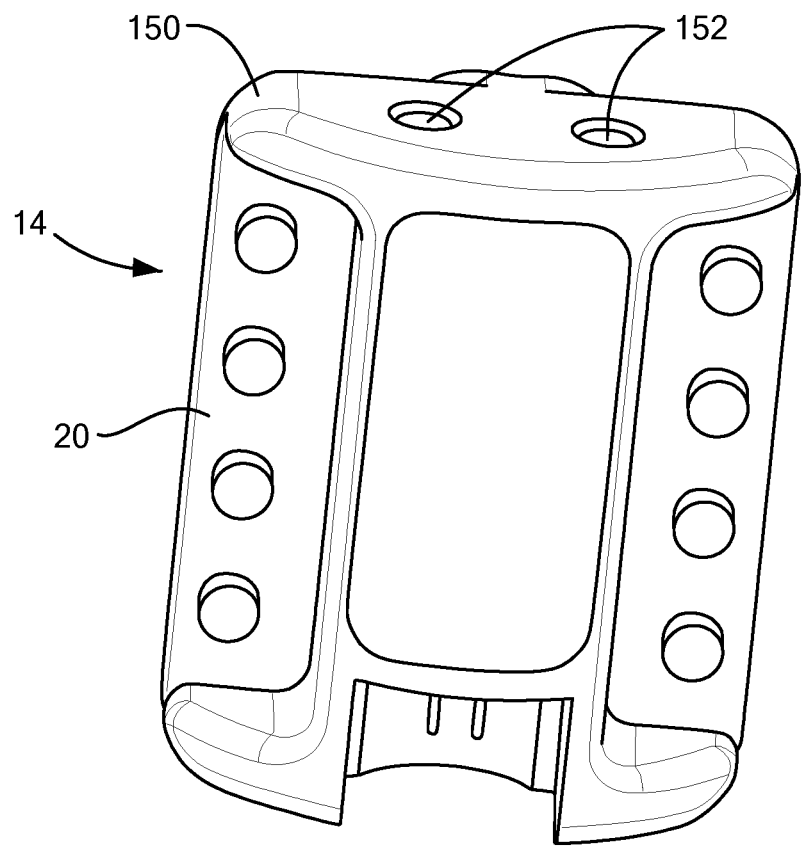
FIG. 26 is a top view of the first brace portion shown in FIG. 1 showing ports.
Figure 27:
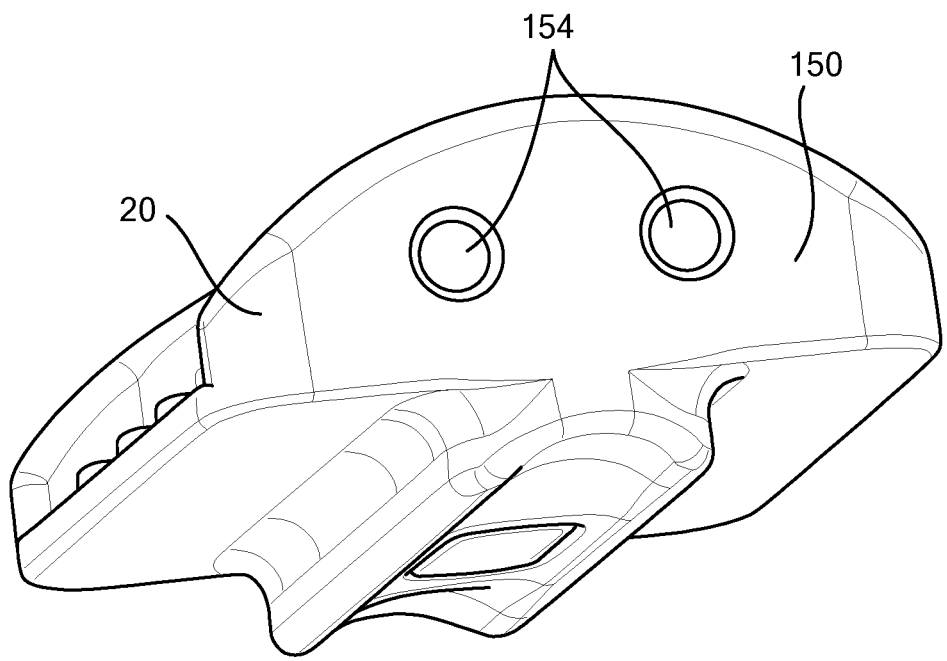
FIG. 27 is a side view of the first brace portion shown in FIG. 26 showing a stopper for the ports.

Now referring to FIG. 26, in order to insert the fluid within the fluid chamber 118, the housing 20 of the first brace portion 14 includes a sidewall 150 defining one or more ports 152, for example a fill port and a vent port, in fluid communication with the fluid chamber 118. The fill port may be used to deposit and adjust the amount of the fluid, e.g., silicone, located within the fluid chamber 118, whereas the vent portion may be used to receive a vacuum to remove any entrapped air from the fluid chamber 118. The removal of air assists in providing the fluid that is free of air bubbles in an effort to obtain accurate hydraulic pressure measurements. As shown in FIG. 27, a stopper 154, for example a ceramic ball, may be disposed within each of the ports 152 to provide a hermetic seal.

Figure 28:
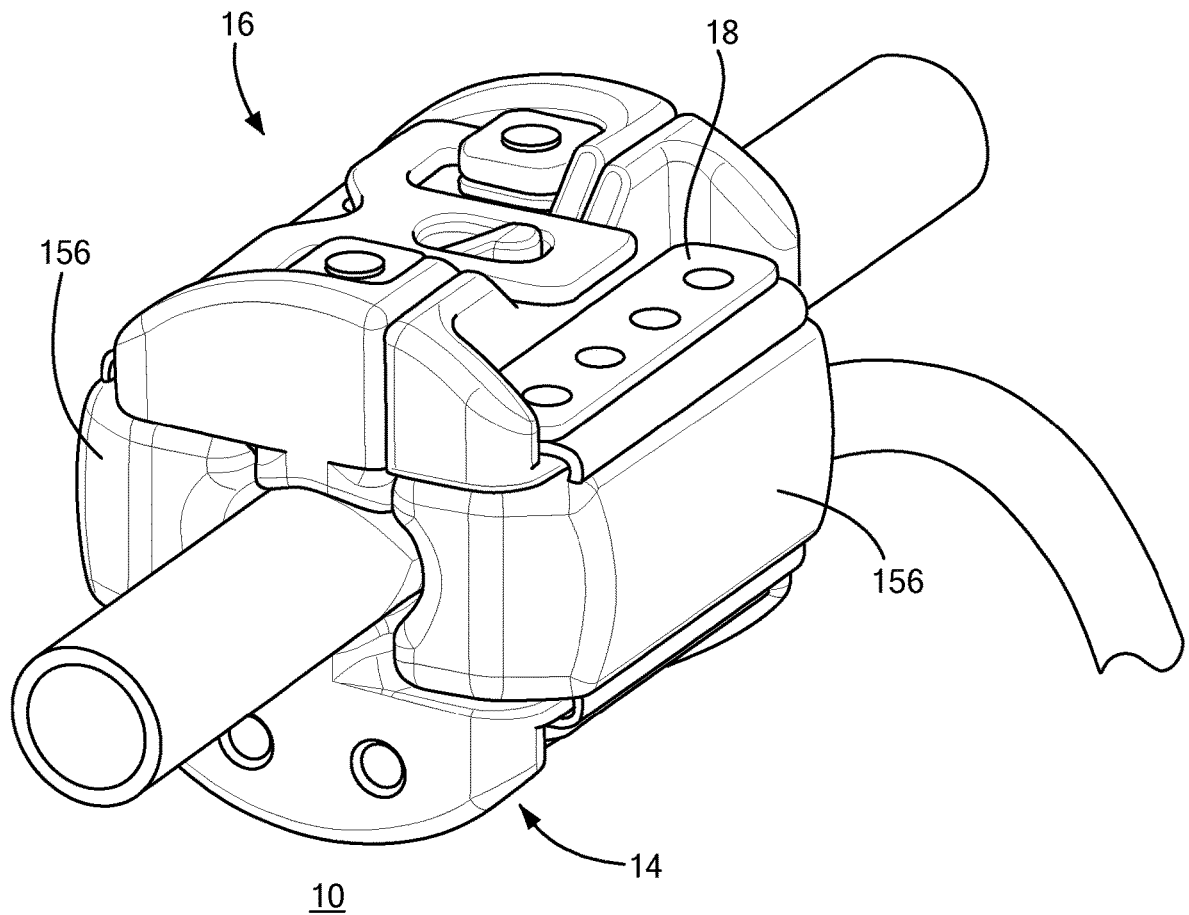
FIG. 28 is a front view of the cuff shown in FIG. 1 showing a casing surrounding the biasing members.
Figure 29:
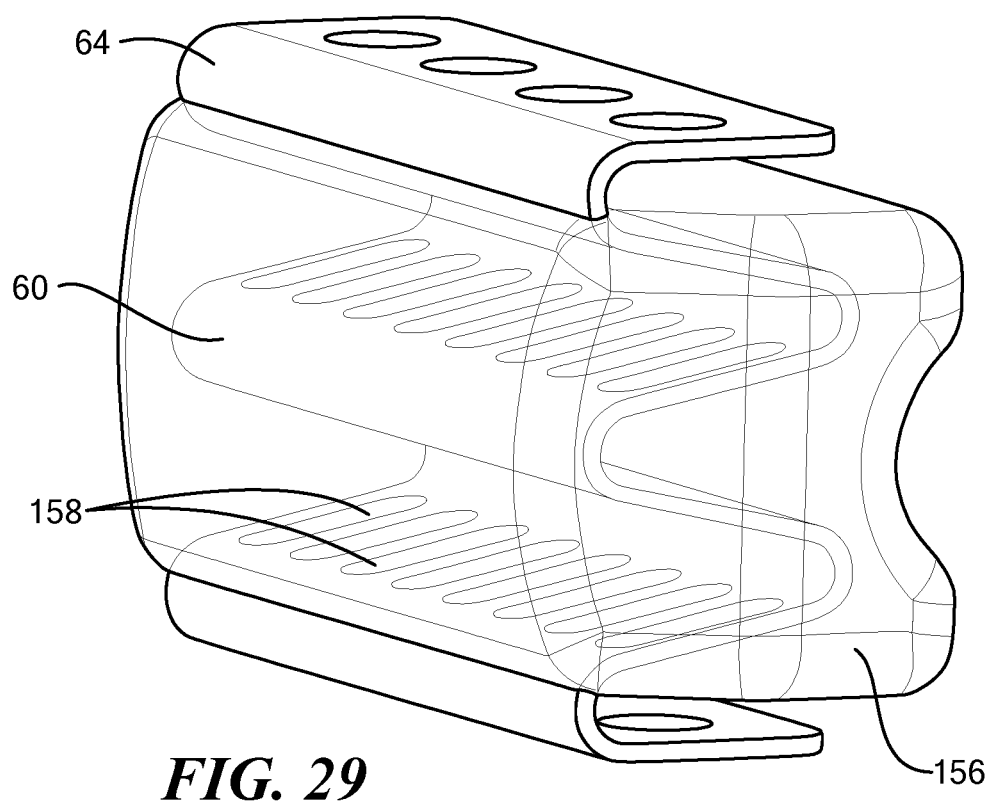
FIG. 29 is outside view of the casing shown in FIG. 28 over molded over the biasing member.
Figure 30:
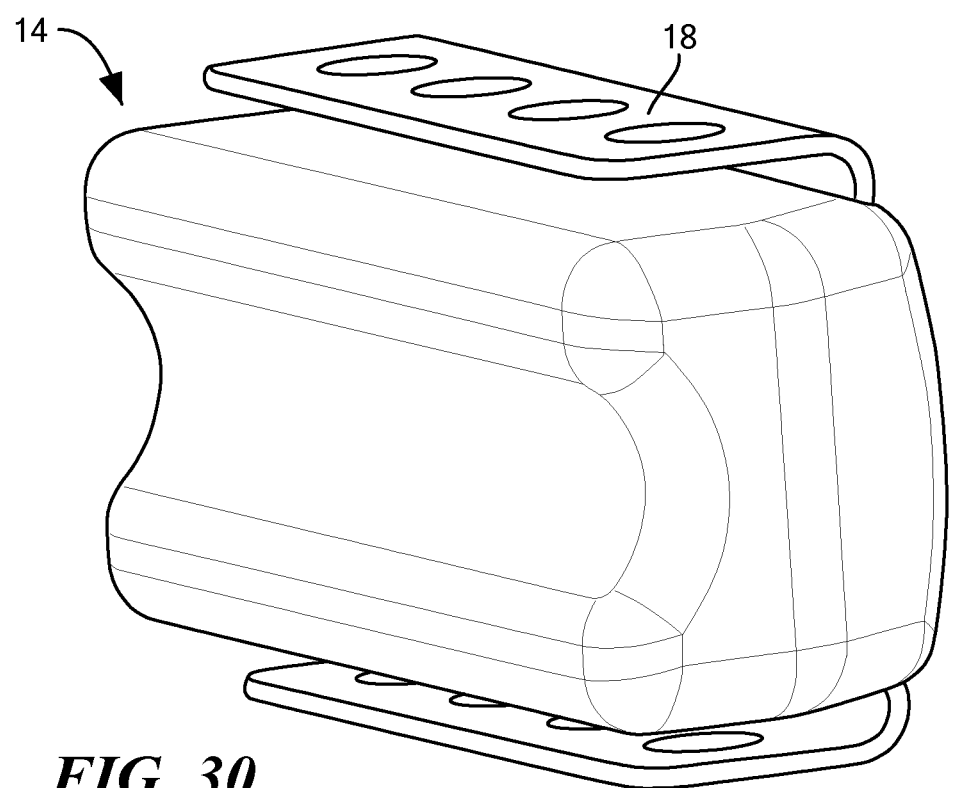
FIG. 30 is an inside view of the casing shown in FIG. 29.

Referring now to FIGS. 28-30, the cuff 10 may include a casing 156 coupled to the first brace portion 14 and/or the second brace portion 16 and surrounding the folds 60 of the biasing members 18 and 64. For example, with reference to FIGS. 29-30, the casing 156 may be an over mold, made of a material such as silicone rubber or another suitable biocompatible material, which is coupled to the biasing members 18 and 64 before the biasing members 18 and 64 are coupled to the first brace portion 14 and/or the second brace portion 16.

Figure 31:
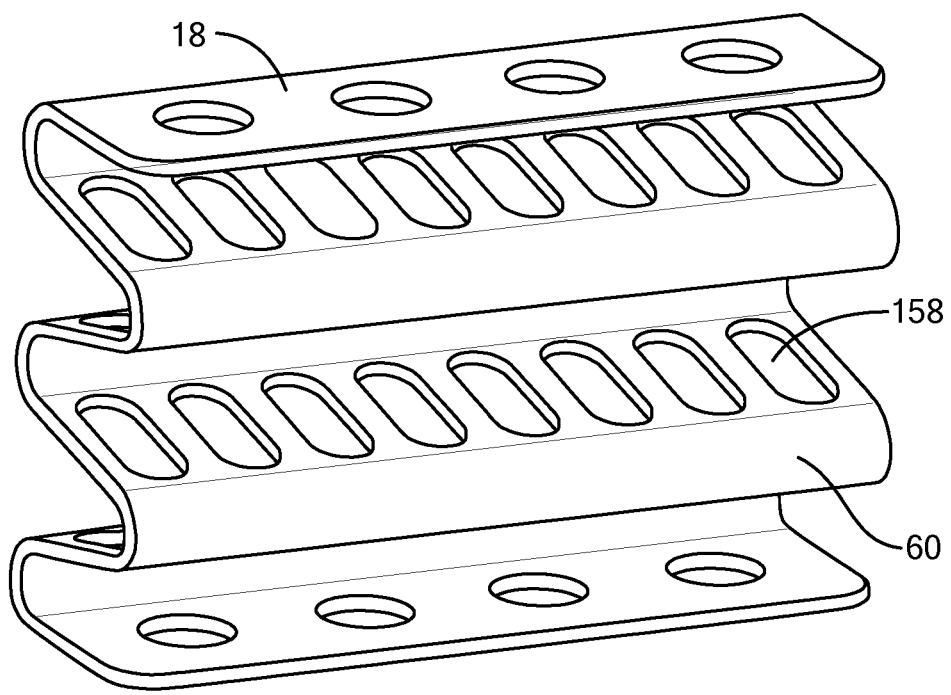
FIG. 31 is a front perspective view of the biasing member shown in FIG. 29.
Figure 32:
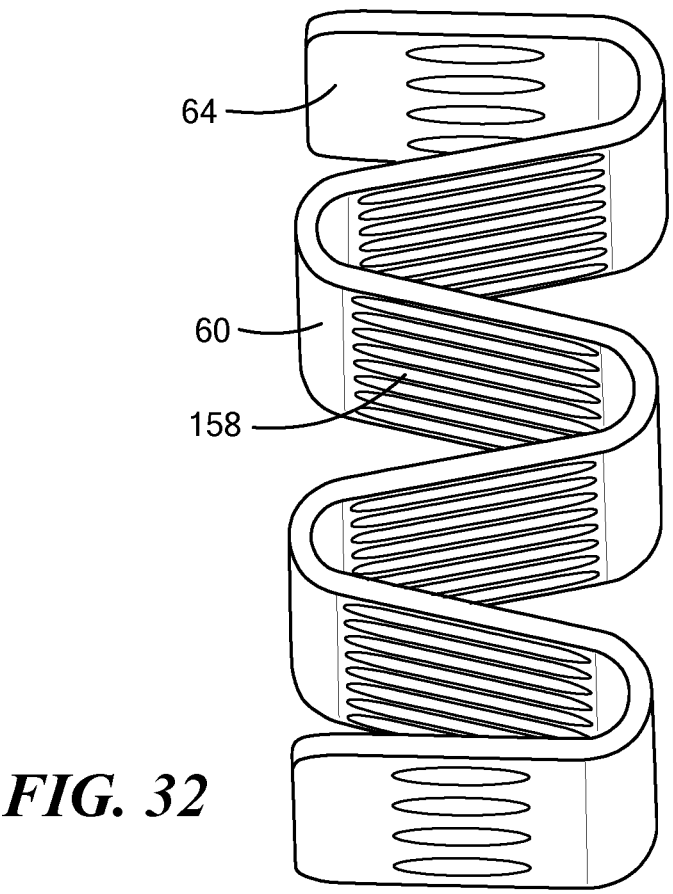
FIG. 32 is a side perspective view of the biasing member shown in FIG. 29.
Figure 33:
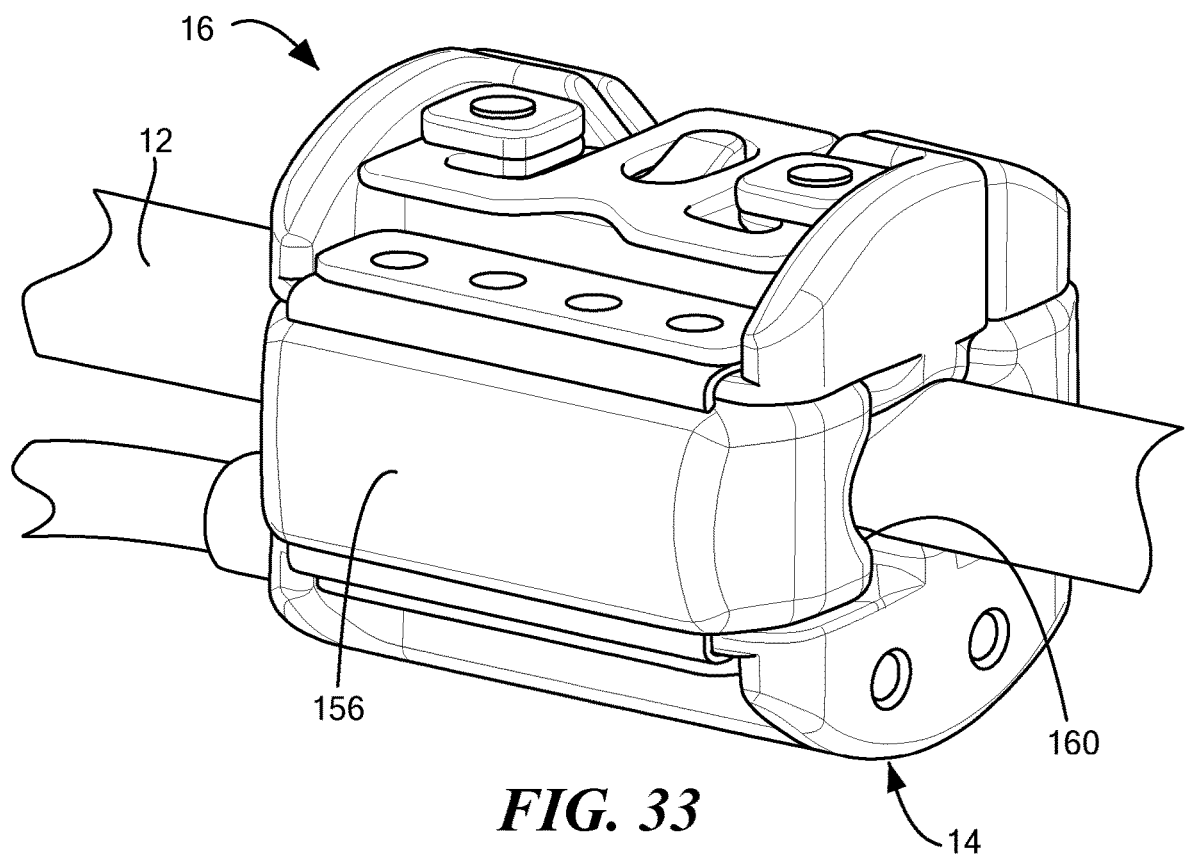
FIG. 33 is a side view of the cuff shown in FIG. 1 showing the casing against a blood vessel.

Referring now to FIGS. 31-32, the biasing members 18 and 64 may define one or more apertures 158 extending along the folds 60 configured to assist in coupling the biasing members 18 and 64 to the first brace portion 14 and/or the second brace portion 16 of the cuff 10 (FIG. 28). Referring to FIG. 33, the casing 156 defines a brace gap 160 between the first brace portion 14 and/or the second brace portion 16 and the blood vessel 12 to limit tissue integration. The blocking of such tissue integration is configured to preserve the mechanical integrity and overall stiffness of the cuff 10.

Figure 34:
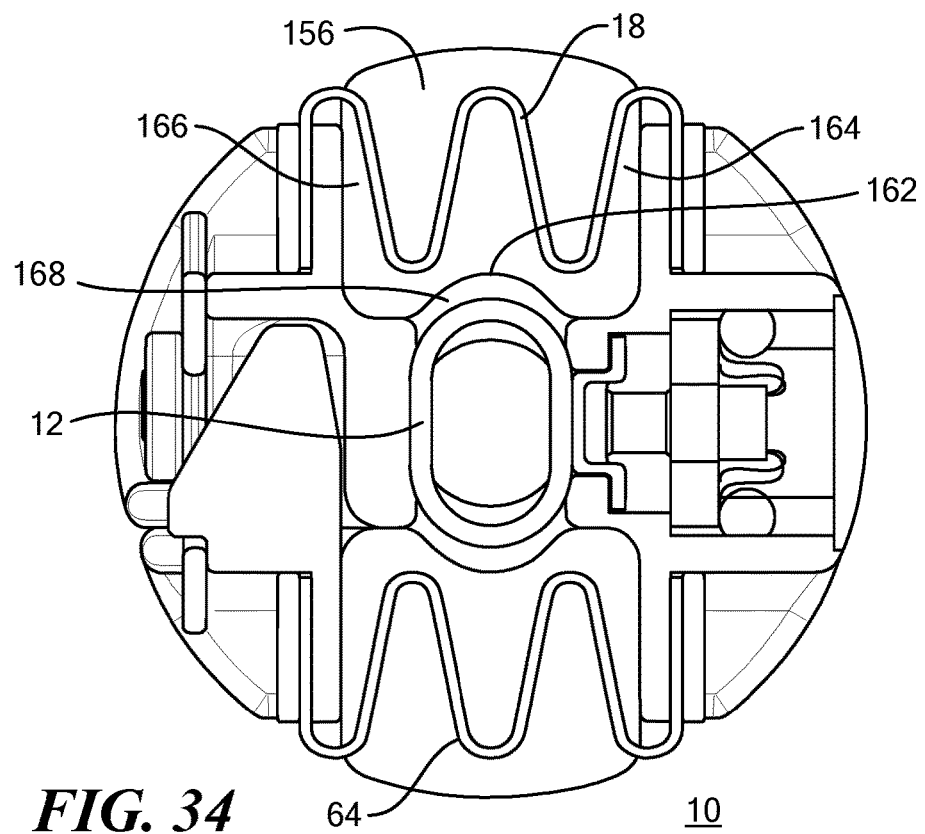
FIG. 34 is a cross-sectional view of the cuff shown in FIG. 33 showing the concavity of the casing.

Referring now to FIG. 34, the casing 156 may include a concave portion 162 with respect to a pair of sidewalls 164 and 166 of the casing 156 which assists in centering the blood vessel 12 between the first brace portion 14 and/or the second brace portion 16. As such, the blood vessel 12 is less prone to moving between the first brace portion 14 and the second brace portion 16 when a transverse or tilting load is applied to the cuff 10. In addition, the casing 156 may define a gap 168 between the casing 156 and the blood vessel 12 to accommodate blood vessels of various sizes. Naturally, the size of the gap 168 may vary depending upon the size of the blood vessel 12.

Figure 35:
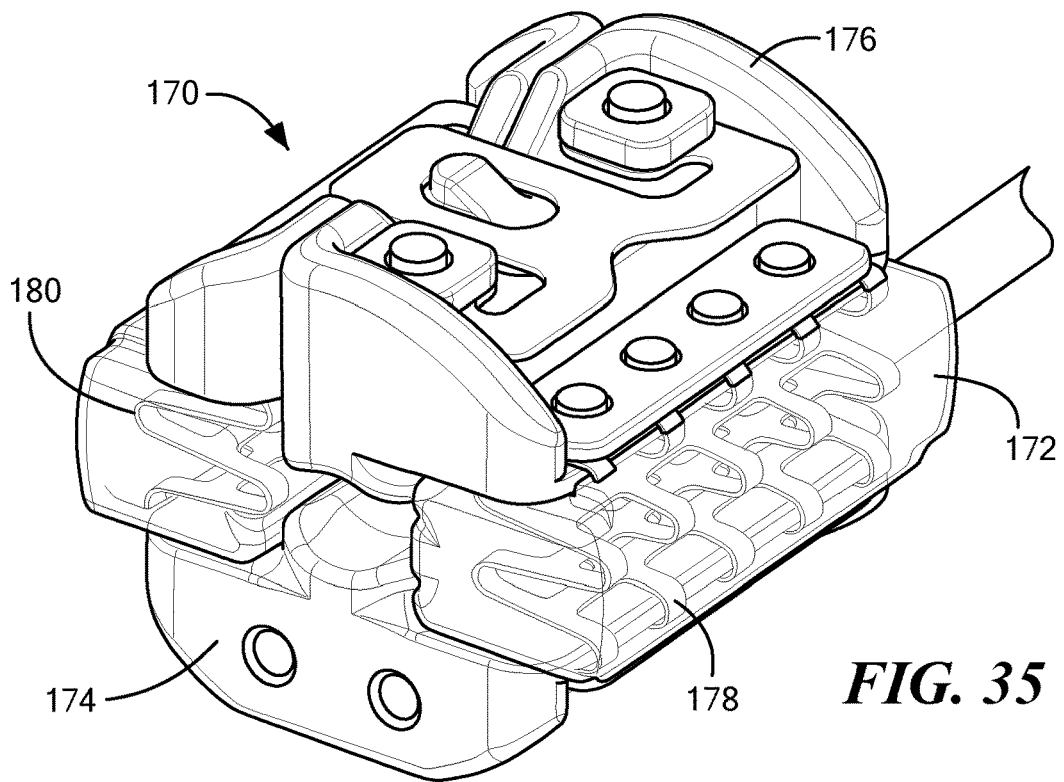
FIG. 35 is a front perspective view of an extravascular cuff constructed in accordance with the principles of the present application showing biasing members with an over molded casing.

Referring now to FIG. 35 in which a perspective view of another exemplary implantable extravascular cuff 170 which operates in a manner similar to the cuff 10 including at least partially surrounding the blood vessel 12 (FIG. 1) without breaching or significantly obstructing the blood vessel 12, to measure blood pressure and/or perform additional or alternative medical diagnostics. The cuff 170 includes a casing 172 provided between a first brace portion 174 and a second brace portion 176 for surrounding select portions of the blood vessel 12 without necessitating the complete encircling of the blood vessel 12. The casing 172 is provided in a transparent view illustrating a pair of biasing members 178 and 180, respectfully, within the casing which couple the first brace portion 174 and the second brace portion 176 to each other. The casing 172 occupies space between the first brace portion 174 and the second brace portion 176 to limit tissue integration within gaps of the biasing members 178 and 180 which might otherwise effect the mechanical properties of the cuff 170. The biasing members 178 and 180 allow for a clearance between the casing 172 and the blood vessel 12 to accommodate variations in blood vessel size. Similar to that described above with respect to the casing 156, the casing 172 may be an over mold, made of a material such as silicone rubber or another suitable biocompatible material, which is coupled to the biasing members 178 and 180 before the biasing members 178 and 180 are coupled to the first brace portion 174 and the second brace portion 176.

Figure 36:
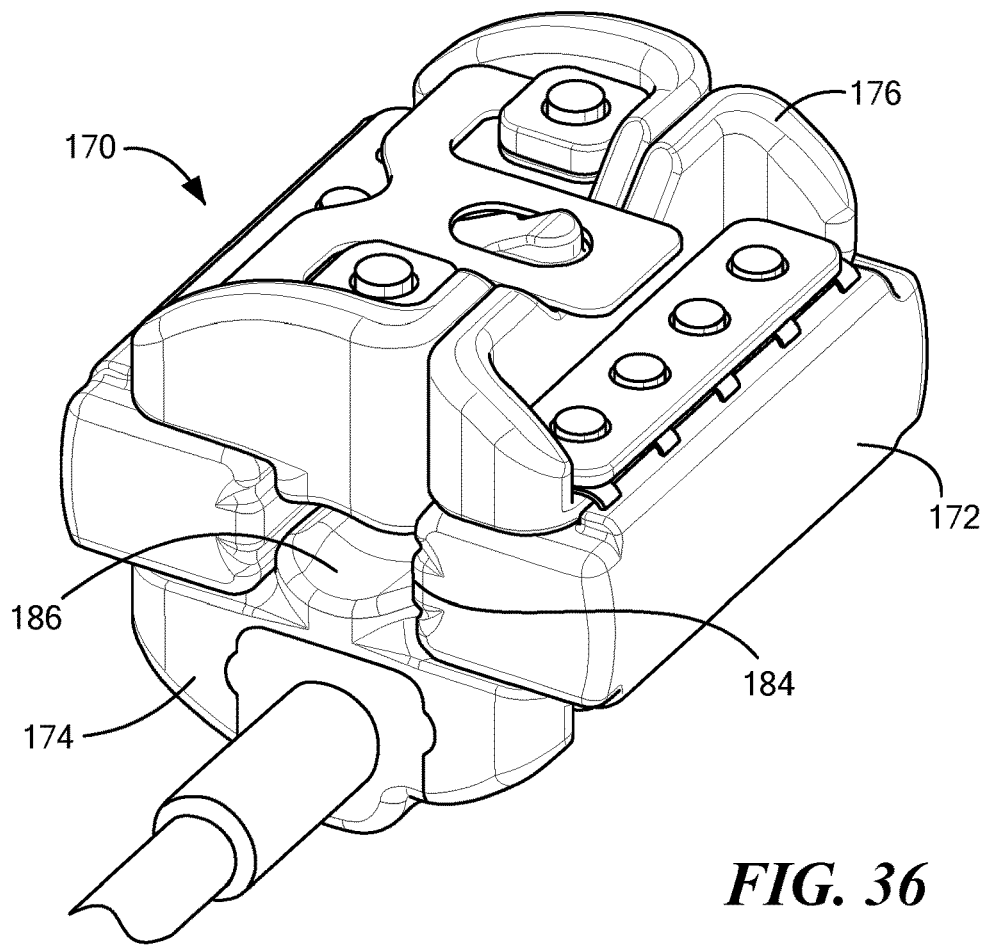
FIG. 36 is the perspective view of FIG. 35 showing the casing member.

Referring now to FIG. 36, in one configuration the cuff 170 includes the casing 172 having a pair of protrusions 182 and 184 which act as lateral restraints to maintain alignment of the blood vessel 12 between the pair of protrusions 182 and 184 when disposed there between. The protrusions 182 and 184 are on opposing sides of a concave abutment structure 186 which assists in preventing movement of the blood vessel 12 when there is momentum or a transverse load applied to the cuff 170.

Figure 37:
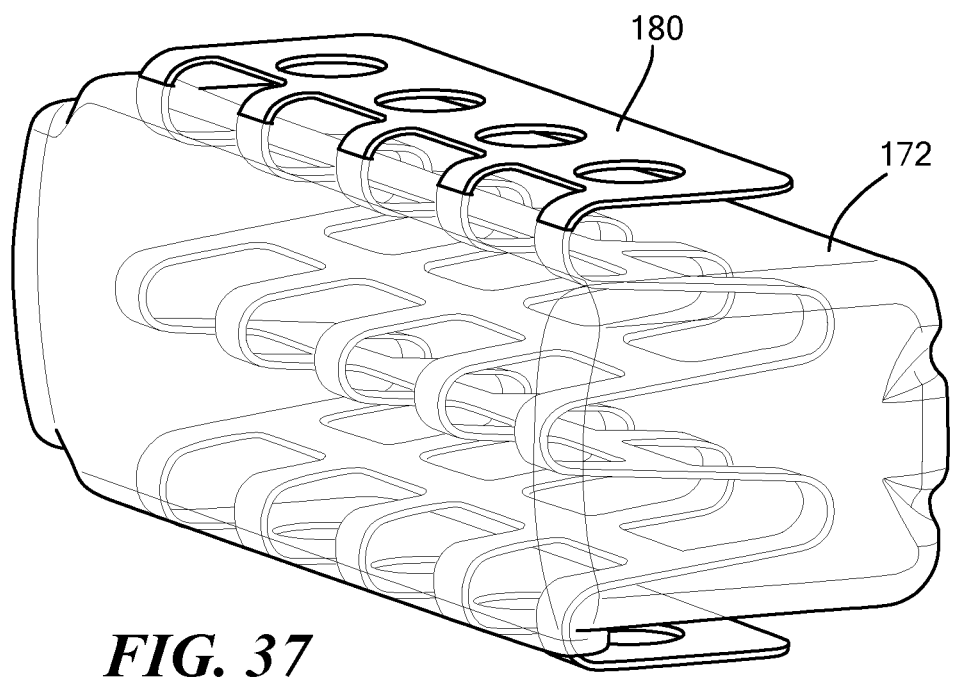
FIG. 37 is an outside view showing the casing member over molded over the biasing member.
Figure 38:
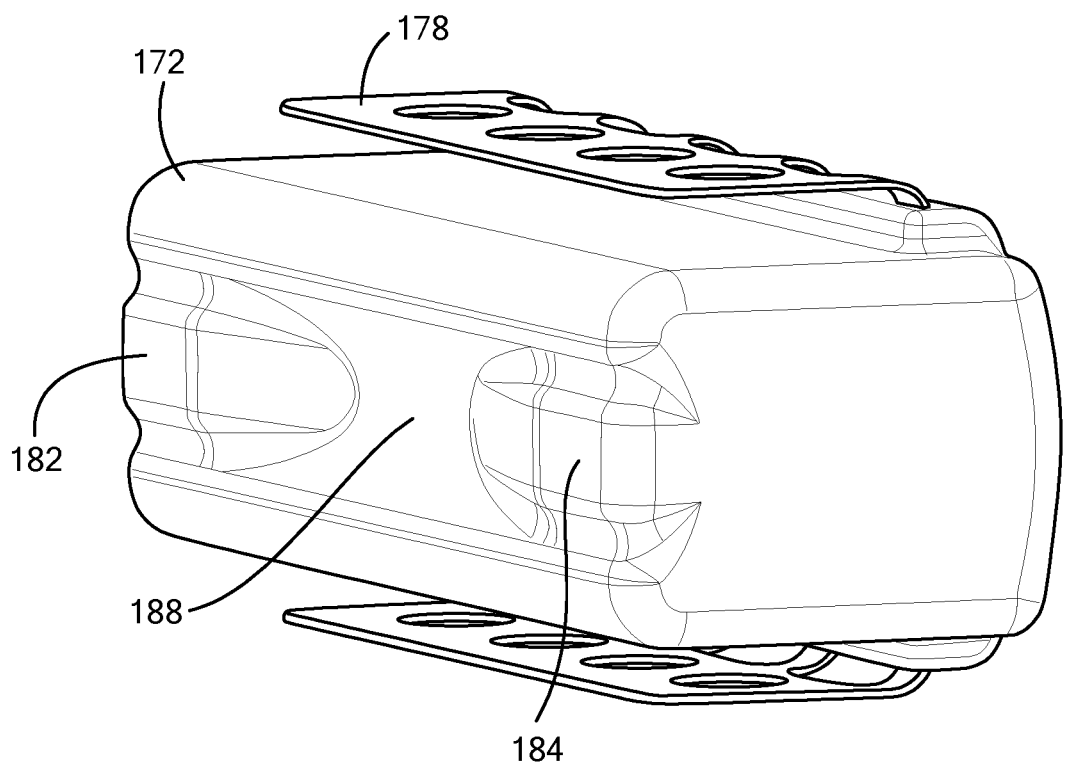
FIG. 38 is an inside view of the casing member shown in FIG. 27 showing the protrusions.

Referring now to FIGS. 37 and 38, the casing 172 includes the biasing members 178 and 180 extending within and around the casing 172. The biasing members 178 and 180 include the properties described above with respect to the biasing members 18 and 64. FIG. 38 depicts the protrusions 182 and 184 protruding from a central region 188 of the casing 172 to provide the lateral restraint.

Figure 39:
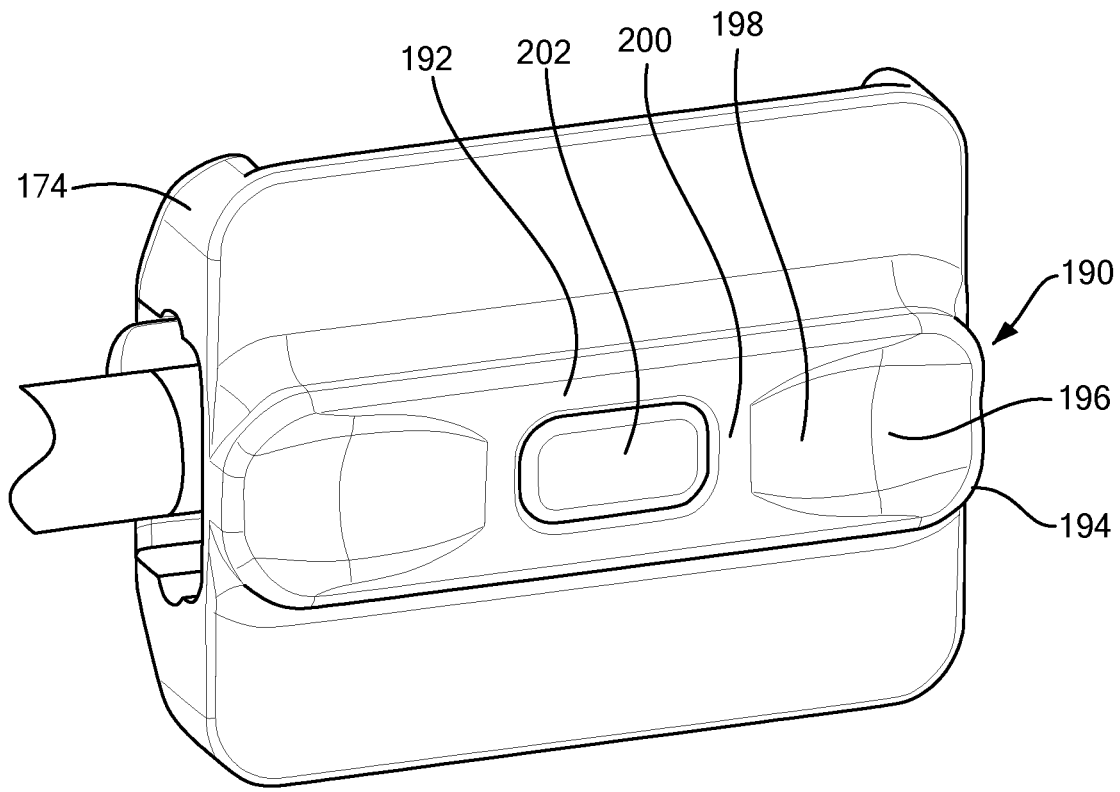
FIG. 39 is an inside perspective view of an abutment structure of an inner wall of the first brace portion shown in FIG. 34.
Figure 40:
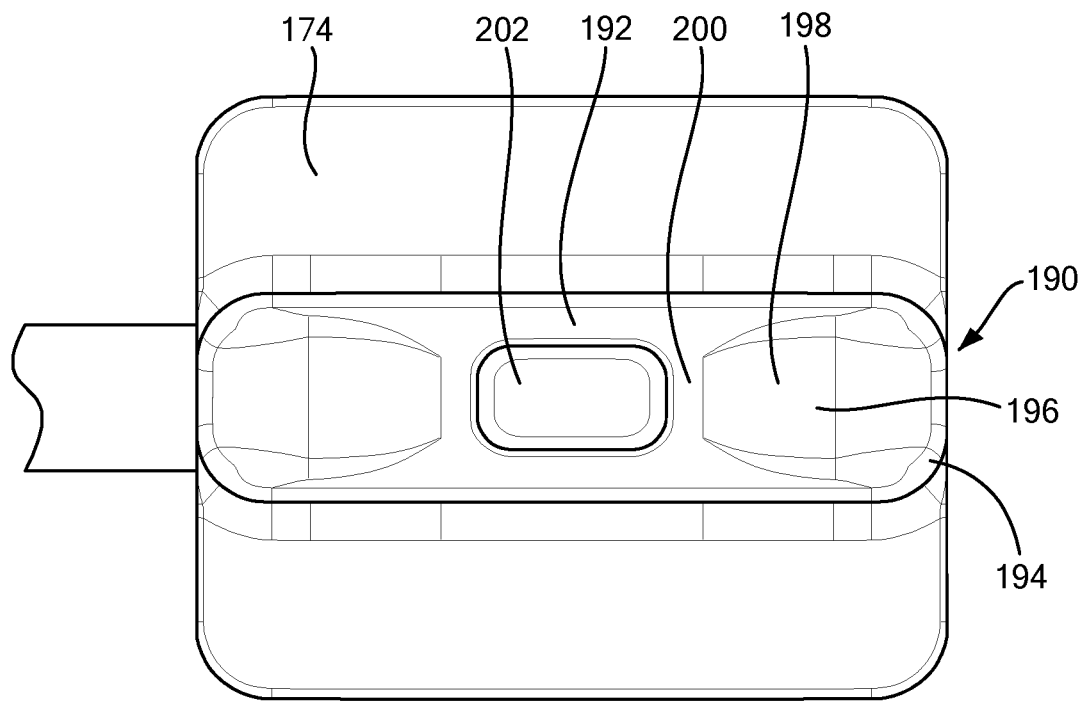
FIG. 40 is an inside side view of the abutment structure shown in FIG. 39.

Referring now to FIGS. 39 and 40, an abutment structure 190, i.e., inner wall, of the first brace portion 174 may define a blood vessel securing region 192 sized and shaped to receive the blood vessel 12 therein. Although not shown, the second brace portion 176 includes the same features with respect to the first brace portion 174 and the abutment structure 190. The abutment structure 190 may include a textured surface that is polished to assist in providing relief from potential tissue rubbing and/or prevent translational movement.

The blood vessel securing region 192 includes one or more curved regions, such as a pair of curved or rounded edges 194, one or more cylindrical support surfaces 196, and one or more transition regions 198 adapted for contact with the blood vessel wall. The blood vessel securing region 192 may have sufficient depth and curvature to maintain long-term alignment of the housing axis with an axis of the blood vessel 12 to prevent misalignment due to rotational movement. The rounded edges 194 define a perimeter around the abutment structure 190. The cylindrical support surface 196 is disposed between the rounded edges 194 at one or both ends of the abutment structure 190. The transition regions 198 extend between the cylindrical support surfaces 196 and a centralized region 200 that is relatively flat or planar. The transition regions 198 form a partially square shape adjacent the centralized region 200 which differs from the relatively obround shape of the transitions regions 76 discussed above. The planar surface of the centralized region 200 is configured to communicate with a flattened portion of a blood vessel wall.

When the cuff 170 is used as a blood pressure sensor, the transitional geometry exhibited by the transition regions 198 is adapted to minimize stress imposed on the blood vessel 12 in undergoing a forced transition from a circular geometry to a constrained flattening of the blood vessel for achieving applanation and accurate blood pressure transduction through the blood vessel wall to a diaphragm 202. The design of the abutment structure 190 allows the cuff 170 to least partially surround the blood vessel 12 without overly constraining the blood vessel 12 when obtaining the blood pressure measurements or performing alternative medical diagnostics. The diaphragm 202 operates in the manner described above with respect to the diaphragm 122.

It will be appreciated by persons skilled in the art that the present application is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the application, which is limited only by the following claims.

What is claimed is:

1. An implantable extravascular pressure sensing system, comprising:
    a cuff including a first brace portion, a second brace portion, and at least two biasing members, each biasing member having a pair of opposing ends with at least one fold disposed between the pair of opposing ends, the pair of opposing ends for each of the at least two biasing members movably coupling the first brace portion and the second brace portion to each other to allow the first brace portion and the second brace portion to move with respect to one another in accordance with a pressure applied by the blood vessel to the first brace portion and the second brace portion, the first brace portion defining a fluid chamber, the first brace portion also defining a recessed aperture that is proximate the fluid chamber where the recessed aperture is in fluid communication with the fluid chamber;
    a flexible diaphragm coupled to the fluid chamber and sealing the recessed aperture;
    a fluid disposed within the fluid chamber for exhibiting a hydraulic pressure in communication with the flexible diaphragm; and
    a pressure sensor coupled to the first brace portion, the pressure sensor being configured to measure a change in the hydraulic pressure when a force is imparted on the flexible diaphragm.

2. The system of claim 1, wherein the flexible diaphragm includes a body having a surface defining an exterior wall of the first brace portion and a skirt surrounding the body.

3. The system of claim 1, wherein the flexible diaphragm is made of a polyurethane material and includes a planar surface adapted to communicate with a flattened portion of a blood vessel wall.

4. The system of claim 1, wherein the fluid disposed within the fluid chamber is a silicone fluid.

5. The system of claim 1, wherein the pressure sensor is a micro-electromechanical system sensor.

6. The system of claim 1, further comprising an electronic circuit disposed between the flexible diaphragm and the fluid chamber, the electronic circuit defining a first aperture therethrough.

7. The system of claim 6, further comprising a sealing member adjacent the flexible diaphragm, the sealing member creating a seal when coupled to the flexible diaphragm to prevent fluid from leaking from the first aperture.

8. The system of claim 1, wherein the first brace portion includes a sidewall defining a plurality of ports in fluid communication with the fluid chamber.

9. The system of claim 1, wherein the first brace portion defines a blood vessel securing region at least partially surrounding the flexible diaphragm.

10. The system of claim 1, wherein the opposing ends of each of the at least two biasing members defining a plurality of apertures and the first brace portion includes a first plurality of protrusions and the second brace portion includes a second plurality of protrusions, the plurality of apertures being sized to receive the first and second plurality of protrusions to secure each at least two biasing members to the first brace portion and the second brace portion.

11. The system of claim 1, wherein each at least one two biasing members are releasably engageable to the first brace portion and the second brace portion.

* * * * *